US012534688B2

(12) United States Patent
Ahuja et al.

(10) Patent No.: US 12,534,688 B2
(45) Date of Patent: Jan. 27, 2026

(54) FABRIC SOFTENER COMPOSITION COMPRISING A BETAINE ESTER AND A FATTY CO-SOFTENER

(71) Applicant: Conopco, Inc., Englewood Cliffs, NJ (US)

(72) Inventors: Ritu Ahuja, Amnios (SG); Olivier Back, Lyons (FR); Christopher Boardman, Llandyrnog (GB); Jean-Christophe Castaing, Sèvres (FR); Konstantin Nikolaev Golemanov, Paris (FR); David Stephen Grainger, Chester (GB); Sergio Mastroianni, Lyons (FR); Hugh Rieley, Wirral (GB)

(73) Assignee: Conopco, Inc., Englewood Cliffs, NJ (US)

( * ) Notice: Subject to any disclaimer, the term of this patent is extended or adjusted under 35 U.S.C. 154(b) by 656 days.

(21) Appl. No.: 17/766,268

(22) PCT Filed: Sep. 28, 2020

(86) PCT No.: PCT/EP2020/077107
§ 371 (c)(1),
(2) Date: Apr. 4, 2022

(87) PCT Pub. No.: WO2021/069249
PCT Pub. Date: Apr. 15, 2021

(65) Prior Publication Data

US 2022/0396749 A1 Dec. 15, 2022

(30) Foreign Application Priority Data

Oct. 7, 2019 (EP) .................................... 19306301

(51) Int. Cl.

| | |
|---|---|
| ***C11D 1/62*** | (2006.01) |
| ***C07C 229/22*** | (2006.01) |
| ***C11D 3/00*** | (2006.01) |
| ***C11D 3/20*** | (2006.01) |
| ***C11D 3/30*** | (2006.01) |

(52) U.S. Cl.
CPC .......... *C11D 3/0015* (2013.01); *C07C 229/22* (2013.01); *C11D 3/0026* (2013.01); *C11D 3/2013* (2013.01); *C11D 3/2079* (2013.01); *C11D 3/2093* (2013.01); *C11D 3/30* (2013.01)

(58) Field of Classification Search
CPC ......... C11D 1/62; C11D 3/001; C11D 3/2013; C11D 3/3927; C11D 2111/12
See application file for complete search history.

(56) References Cited

U.S. PATENT DOCUMENTS

| | | | | |
|---|---|---|---|---|
| 4,676,547 | A | 6/1987 | Spillman | |
| 5,543,066 | A | 8/1996 | Weissen et al. | |
| 5,858,960 | A * | 1/1999 | Conroy | C11D 3/0015 510/521 |
| 6,218,354 | B1 | 4/2001 | Demeyere et al. | |
| 8,851,982 | B2 | 10/2014 | Englman et al. | |
| 2011/0300085 | A1* | 12/2011 | Courbon | A61K 8/06 514/159 |
| 2012/0246838 | A1 | 10/2012 | Garduno | |
| 2013/0338210 | A1* | 12/2013 | Manoharan | C07C 323/25 549/341 |
| 2014/0004565 | A1* | 1/2014 | Rossomando | C12N 15/1137 435/70.3 |
| 2014/0099666 | A1* | 4/2014 | Rossomando | C12N 15/111 435/68.1 |
| 2014/0315779 | A1 | 10/2014 | Zander | |
| 2017/0342345 | A1 | 11/2017 | Sivik et al. | |
| 2018/0093936 | A1 | 4/2018 | Back et al. | |
| 2022/0290075 | A1 | 9/2022 | Ahuja et al. | |
| 2022/0396749 | A1 | 12/2022 | Ahuja et al. | |

FOREIGN PATENT DOCUMENTS

| | | | |
|---|---|---|---|
| DE | 3402146 | * | 7/1985 |
| EP | 0922755 | A1 | 6/1999 |
| IL | 132332 | A | 2/2003 |
| JP | 09111660 | | 4/1997 |
| JP | 9-195167 | | 7/1997 |
| WO | 96/09276 | * | 3/1996 |
| WO | 199708284 | A1 | 3/1997 |
| WO | WO2007078782 | | 7/2007 |
| WO | 2016014802 | A1 | 1/2016 |
| WO | WO2018033607 | | 2/2018 |

OTHER PUBLICATIONS

Search Report and Written Opinion in EP19306301; Mar. 23, 2020.
Search Report and Written Opinion in EP19306300; Mar. 24, 2020.
Search Report and Written Opinion in PCTEP2020077064; Dec. 30, 2020.
Search Report and Written Opinion in PCTEP2020077107; Dec. 9, 2020.
European Search Report and Written Opinion in corresponding European Patent Application No. EP19306301 dated Mar. 23, 2020 (7 pages).

* cited by examiner

*Primary Examiner* — Charles I Boyer
(74) *Attorney, Agent, or Firm* — Carter, DeLuca & Farrell, LLP; George Likourezos; Bret P. Shapiro

(57) ABSTRACT

A fabric softener composition comprising: a. 1 to 20 wt. % ionic compound of general formula I: (I) wherein b. 0.1 to 20 wt. % fatty co-softener; and c. Water.

(I)

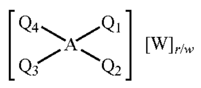

11 Claims, No Drawings

FABRIC SOFTENER COMPOSITION COMPRISING A BETAINE ESTER AND A FATTY CO-SOFTENER

FIELD OF THE INVENTION

The present invention is concerned with a fabric softener comprising a novel softening compound and fatty co-softener.

BACKGROUND OF THE INVENTION

Fabric softeners otherwise known as fabric conditioners have been on the market for many years. The softening agents have developed over the years. A commonly used softening agent are quaternary ammonium cationic surfactants, in particular ester linked quaternary ammonium compounds.

However, there is a need for improved softening ingredients. More effective softening allows for lower dosing or more concentrated products, which in turn leads to many environmental benefits.

SUMMARY OF THE INVENTION

In a first aspect of the present invention is provided a fabric softener composition comprising:

a. 1 to 20 wt. % ionic compound of general formula I:

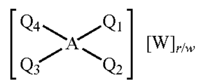

(I)

wherein

A is a tetravalent linker selected from the group consisting of A-1 to A-6

A-1

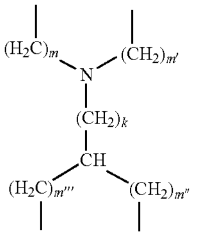

A-2

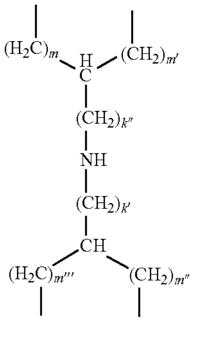

-continued

A-3

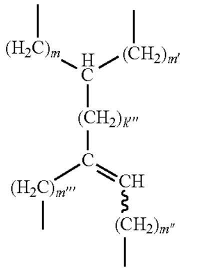

A-4

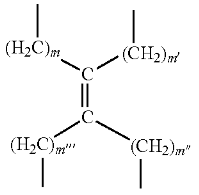

A-5

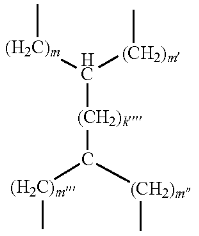

A-6

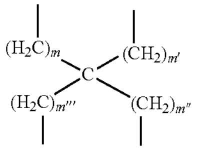

$Q_1$ to $Q_4$, which may be identical or different from each other, are selected from the group consisting of hydrogen, R and X, and W is an anion or an anionic group bearing w negative charges and r is the number of substituents Q1 to Q4 which are represented by a group X, wherein R, which may be the same or different at each occurrence, is a $C_5$-$C_{27}$ aliphatic group, m, m', m" and m'", which may be the same or different at each occurrence, are 0, 1, 2 or 3, k, k' k", k'" and k"", which may be the same or different, are 0, 1, 2 or 3, and X, which may be the same or different at each occurrence, is represented by formula II

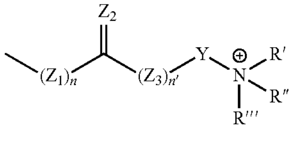

(II)

wherein $Z_1$, $Z_2$ and $Z_3$, which may be the same or different, are O, S or NH, Y is a divalent $C_1$-$C_6$ aliphatic radical, R', R" and R'", which may be the same or different, are hydrogen or a $C_1$ to $C_4$ alkyl group, n and n' are 0 or 1 with the sum of n+n' being 1 or 2, wherein at least one of $Q_1$ to $Q_4$ is represented by X and at least two of groups $Q_1$ to $Q_4$ are represented by R, which groups R may be the same or different at each occurrence, and wherein, if the ionic compound is such that (i) A is represented by A-6 with m, m', m" and m"' equal to 0, (ii) one and only one of $Q_1$ to $Q_4$ is represented by a substituent X and n in the substituent X is equal to 0 and (iii) two and only two of $Q_1$ to $Q_4$ are represented by substituents R, then the difference of the number of carbon atoms of the two substituents R is 0, 1, 3 or more than 3.

b. 0.1 to 20 wt. % fatty co-softener; and c. Water.

In a second aspect of the present invention is provided the use of a fabric softener formulation as described herein, to soften fabrics.

DETAILED DESCRIPTION OF THE INVENTION

These and other aspects, features and advantages will become apparent to those of ordinary skill in the art from a reading of the following detailed description and the appended claims. For the avoidance of doubt, any feature of one aspect of the present invention may be utilised in any other aspect of the invention. The word "comprising" is intended to mean "including" but not necessarily "consisting of" or "composed of." In other words, the listed steps or options need not be exhaustive. It is noted that the examples given in the description below are intended to clarify the invention and are not intended to limit the invention to those examples per se. Similarly, all percentages are weight/weight percentages unless otherwise indicated. Except in the operating and comparative examples, or where otherwise explicitly indicated, all numbers in this description indicating amounts of material or conditions of reaction, physical properties of materials and/or use are to be understood as modified by the word "about". Numerical ranges expressed in the format "from x to y" are understood to include x and y. When for a specific feature multiple preferred ranges are described in the format "from x to y", it is understood that all ranges combining the different endpoints are also contemplated.

Softening Compound:

The fabric softener compositions of the present invention comprise softening compounds, the softening compound is a novel ionic compound. The novel ionic compounds have the general formula (I):

(I)

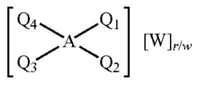

wherein A is a tetravalent linker selected from the group consisting of A-1 to A-6,

A-1

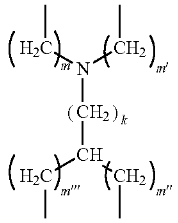

A-2

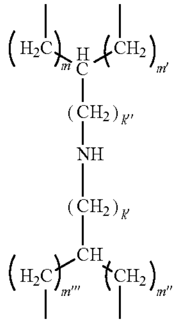

A-3

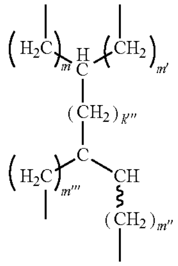

A-4

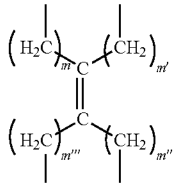

A-5

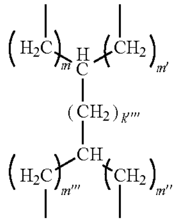

A-6

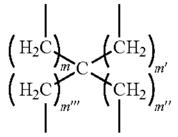

$Q_1$ to $Q_4$, which may be identical or different from each other, are selected from the group consisting of hydrogen, R and X, and W is an anion or an anionic group bearing w negative charges and r is the number of substituents $Q_1$ to $Q_4$ which are represented by a group X, wherein R, which may be the same or different at each occurrence, is a $C_5$-$C_{27}$ aliphatic group, preferably a $C_6$ to $C_{24}$ aliphatic group, m, m', m'' and m''', which may be the same or different at each occurrence, are 0, 1, 2 or 3, k, k', k'', k''' and k'''', which may be the same or different, are 0, 1, 2 or 3, and X, which may be the same or different at each occurrence, is represented by formula II (II)

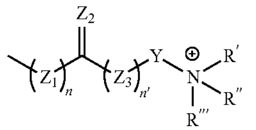

wherein $Z_1$, $Z_2$ and $Z_3$, which may be the same or different, are O, S or NH, Y is a divalent $C_1$-$C_6$ aliphatic radical, R', R'' and R''', which may be the same or different, are hydrogen or a $C_1$ to $C_4$ alkyl group, n and n' are 0 or 1 with the sum of n+n' being 1 or 2, wherein at least one of $Q_1$ to $Q_4$ is represented by X and at least two of groups $Q_1$ to $Q_4$ are represented by R, which groups R may be the same or different at each occurrence, and wherein, if the ionic compound is such that (i) A is represented by A-6 with m, m', m'' and m''' equal to 0, (ii) one and only one of $Q_1$ to $Q_4$ is represented by a substituent X and n in the substituent X is equal to 0 and (iii) two and only two of $Q_1$ to $Q_4$ are represented by substituents R, then the difference of the number of carbon atoms of the two substituents R is 0, 1, 3 or more than 3.

Suitable anions or anionic groups W are e.g. halides such as chloride, fluoride, bromide or iodide, methyl sulfate or methosulfate anion ($CH_3$—$OSO_3^-$), sulfate anion, hydrogensulfate anion ($HSO_4^-$) or an organic carboxylate anion such as acetate, propionate, benzoate, tartrate, citrate, lactate, maleate or succinate.

m, m', m'', m''', which may be the same or different at each occurrence, are preferably 0, 1 or 2, even more preferably 0 or 1.

k, k', k''' and k'''', which may be the same or different, are preferably 0, 1 or 2, even more preferably 0 or 1.

The novel compounds of the present invention are quaternary ammonium derivatives and comprise a tetravalent linker A and four substituents $Q_1$ to $Q_4$ which may be the same or different from each other at each occurrence. At least two of $Q_1$ to $Q_4$ are groups R, i.e. an aliphatic group comprising from 5 to 27, preferably from 6 to 24 carbon atoms.

The aliphatic groups R may be free of any double bond and of any triple bond. Alternatively, the aliphatic groups R may comprise at least one —C═C— double bond and/or at least one —C≡C— triple bond.

The aliphatic groups R are advantageously chosen from alkyl groups, alkenyl groups, alkanedienyl groups, alkanetrienyl groups and alkynyl groups. The aliphatic groups R may be linear or branched. Preferably, the aliphatic groups R are independently chosen from alkyl and alkenyl groups.

More preferably, the aliphatic groups R are independently chosen from alkyl and alkenyl groups, generally from $C_6$-$C_{24}$ alkyl and $C_6$-$C_{24}$ alkenyl groups, very often from $C_6$-$C_{21}$ alkyl and $C_6$-$C_{21}$ alkenyl groups and often from (i) $C_6$-$C_{19}$ alkyl and $C_6$-$C_{19}$ alkenyl groups or from (ii) $C_6$-$C_{17}$ alkyl and $C_6$-$C_{17}$ alkenyl groups. More preferably, R represent an alkyl group, generally a $C_6$-$C_{24}$ alkyl group, very often a $C_6$-$C_{21}$ alkyl group, often a $C_6$-$C_{19}$ alkyl group or a $C_6$-$C_{17}$ alkyl group. Aliphatic groups, in particular alkyl groups, with 10 to 20, preferably 11 to 18 carbon atoms have been found advantageous in certain cases.

Acyclic aliphatic groups, more preferably linear aliphatic groups, still more preferably linear alkyl groups may be mentioned as preferred examples of substituents R.

The number of carbon atoms of R can be even or odd and each group R can have the same number of carbon atoms or the number of carbon atoms of different groups R may be different.

If A is represented by A-6 with m, m', m'' and m''' equal to 0, (ii) one and only one of $Q_1$ to $Q_4$ is represented by a substituent X and n in the substituent X is equal to 0 and (iii) two and only two of $Q_1$ to $Q_4$ are represented by substituents R, then the difference of the number of carbon atoms of the two substituents R is 0, 1, 3 or more than 3.

In the ionic compounds of the present invention at least one of substituents $Q_1$ to $Q_4$ is represented by a group X represented by formula (II) above.

In group X preferably at least one, more preferably at least two and most preferably all three of substituents $Z_1$, $Z_2$ and $Z_3$ are oxygen. Compounds in which all three substituents $Z_1$, $Z_2$ and $Z_3$ are oxygen are esters (n+n' is 1) or carbonate (n+n' is 2) derivatives. n and n' can be 0 or 1 and the sum of n and n' is at least 1, preferably 1 or 2.

R', R'' and R''', which may be the same or different, are preferably hydrogen or a $C_1$ to $C_4$ alkyl group, preferably methyl or ethyl, more preferably methyl. Preferably at least one, more preferably at least two, more preferably all three of R', R'' and R''' are a $C_1$ to $C_4$ alkyl group, preferably methyl or ethyl, most preferably methyl.

Y is preferably an acyclic divalent aliphatic group, more preferably a linear divalent aliphatic group, still more preferably a linear alkanediyl (alkylene) group and preferably has 1 to 6, even more preferably 1 to 4 carbon atoms. In compounds where n' is 1, aliphatic group Y preferably has at least two carbon atoms, in particular 2 to 6 carbon atoms.

In accordance with another preferred embodiment, the compound of the present invention comprises one or two groups X and two and only two groups R.

In a first group of preferred compounds of the present invention, A is represented by A-6, m, m', m'' and m''' are 0, $Z_1$ to $Z_3$ are O and the compounds comprise two groups R and one group X. In a preferred subgroup of this embodiment, n is 0 and n' is 1 or n is 1.

In a second group of preferred compounds, A is represented by A-3 or A-4, m, m', m'', m''' and k''' are 0 and two of substituents $Q_1$ to $Q_4$ are represented by groups X with both X attached to the same carbon atom of linker A and two groups R attached to the same or to different carbon atoms of linker A.

In a third group of preferred compounds, A is represented by A-1, m and m' are 1, m'' and m''' are 0, k is 0 and two substituents $Q_1$ to $Q_4$ are represented by groups X with both groups X being attached to the —$(CH_2)_m$— and —$(CH_2)_{m'}$— groups directly attached to the nitrogen atom of linker A.

In a fourth group of preferred compounds, A is represented by A-2, k' is 0, k'' is 1, m is 1, m', m'' and m''' are 0 and two of substituents $Q_1$ to $Q_4$ are represented by groups X attached to two adjacent carbon atoms of linker A.

In a fifth group of preferred compounds, A is represented by A-5, m, m', m'', m' and k'''' are 0, two of substituents $Q_1$ to $Q_4$ are X with each methine group of linker A carrying one group X and one group R wherein X and R might be the same or different at each occurrence. In a preferred subgroup of this embodiment, n is 1, n' is 0, $Z_2$ and $Z_3$ are O and Y is $CH_2$.

The following compounds of formulae (IV) to (IX) represent particularly preferred groups of compounds in accordance with the present invention (IV)

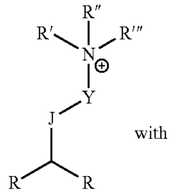

with J being one of $J_1$, $J_2$ or $J_3$ ($J_1$)

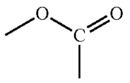

($J_2$)

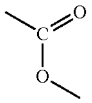

($J_3$)

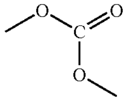

(V)

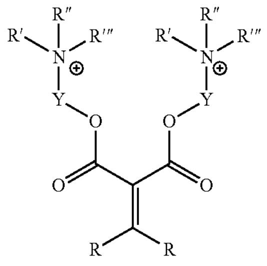

(VI)

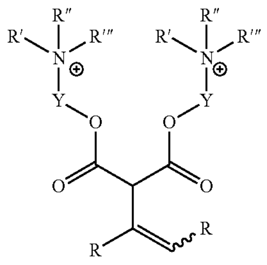

(VII)

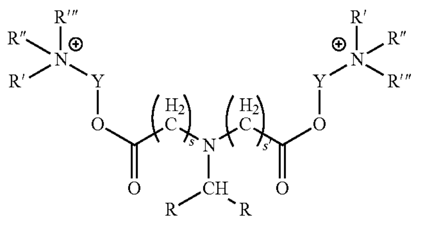

wherein s and s', which may be the same or different, are 0, 1, 2 or 3, (VIII)

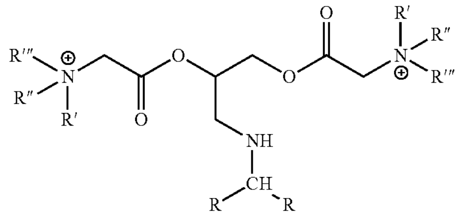

(IX)

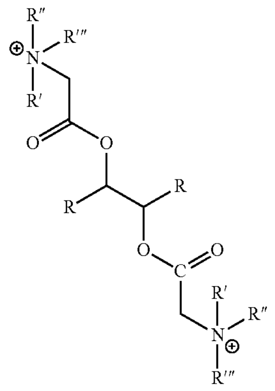

R, R', R", R''' and Y in formulae (IV) to (IX) have the meaning as defined in claim 1 as described hereinbefore.

The ionic compounds for use in the fabric softeners of the present invention can be obtained by a variety of different methods. Preferred processes for the manufacture of the compounds of the present invention include the reaction of an internal ketone of formula R—C(═O)—R, which internal ketone may preferably be obtained by decarboxylative ketonization of a fatty acid, a fatty acid derivative or a mixture thereof. A suitable process for the manufacture of internal ketones following this route is disclosed in US 2018/0093936 to which reference is made for further details.

The synthesis of various compounds for the present invention using internal ketones obtainable as indicated above as starting materials is now described. The process variants described hereinafter show the synthesis of specific compounds and the skilled person will modify the reactants and reaction conditions based on his professional knowledge and taking into account the specific target product of the respective synthesis to manufacture other compounds in accordance with the present invention.

Fabric softening compositions for use in the present invention may be dilute or concentrated fabric softeners. Dilute products typically contain up to about 6%, generally about 1 to 5% by weight of the softening compounds herein described, whereas concentrated products may contain up to about 50 wt. %, preferably from about 5 to about 50%, more preferably from 6 to 25% by weight active. Overall, the products of the invention may contain from 1 to 50 wt. %, preferably from 2 to 25 wt. % of softening compounds, more preferably 2 to 20 wt. % of softening compounds herein described.

Synthesis of Compounds Wherein A is A-6, Exemplary Shown for Compounds of Formula (IV) Wherein J is J1

In a first exemplary process, an internal ketone R—C(═O)—R is first reacted with hydrogen (hydrogenation reaction) to afford a secondary alcohol. This alcohol is then reacted with carbon monoxide through a carbonylation reaction. The carbonylated product which is a carboxylic acid is then subjected to an esterification reaction with a quaternary ammonium salt (for example choline chloride) whereby water is split off and the desired compound of formula (IV) is obtained. Alternatively the carboxylic acid can be first condensed with an aminoalcohol (for example dimethylaminoethanol) through an esterification reaction (with water release) and the obtained aminoester can be quaternized with an alkylating agent.

The reaction scheme for the foregoing sequence of steps is as follows:

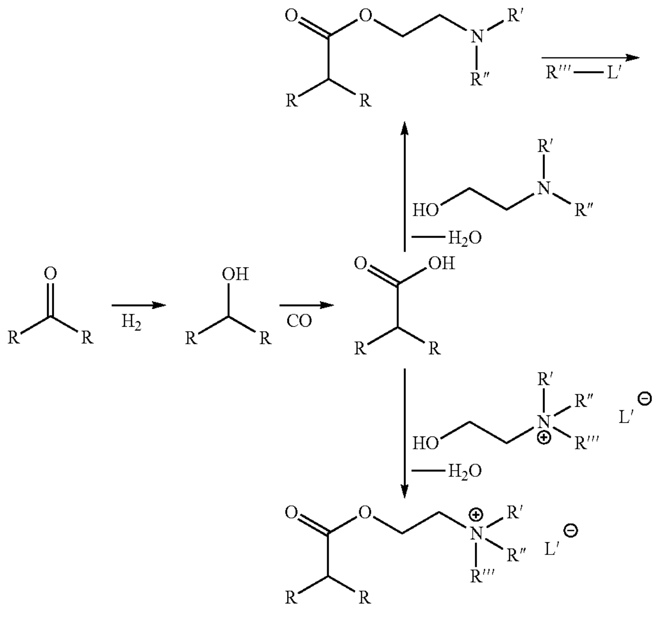

wherein L' is a monovalent leaving group such as e.g. a halide anion (in particular a chloride anion) or a methosulfate group.

The first step in the reaction scheme above comprises a reduction of the internal ketone to the secondary alcohol. This step is followed by a second transformation consisting of the insertion of the carbonyl group to yield the carboxylic acid. Hydrogenation and carbonylation reactions of this general reaction sequence with active hydrogen and carbon monoxide respectively in the presence of suitable catalysts are known to the skilled person and have been described in the literature. The skilled person will select suitable catalysts and reaction conditions based on his professional knowledge taking into account the desired target compound so that no further details need to be given here.

An alternative route to compounds of formula (IV) comprises a hydrocyanation step and consists of the sequence: addition of HCN to the ketone to afford a hydroxynitrile intermediate. This hydroxynitrile is then dehydrated and hydrogenated in one step to afford a nitrile intermediate. This nitrile is then hydrated to afford a carboxylic acid intermediate. This carboxylic acid can be converted to the desired quaternary compound following the same way as described above. The reaction scheme for the foregoing sequence of steps is as follows:

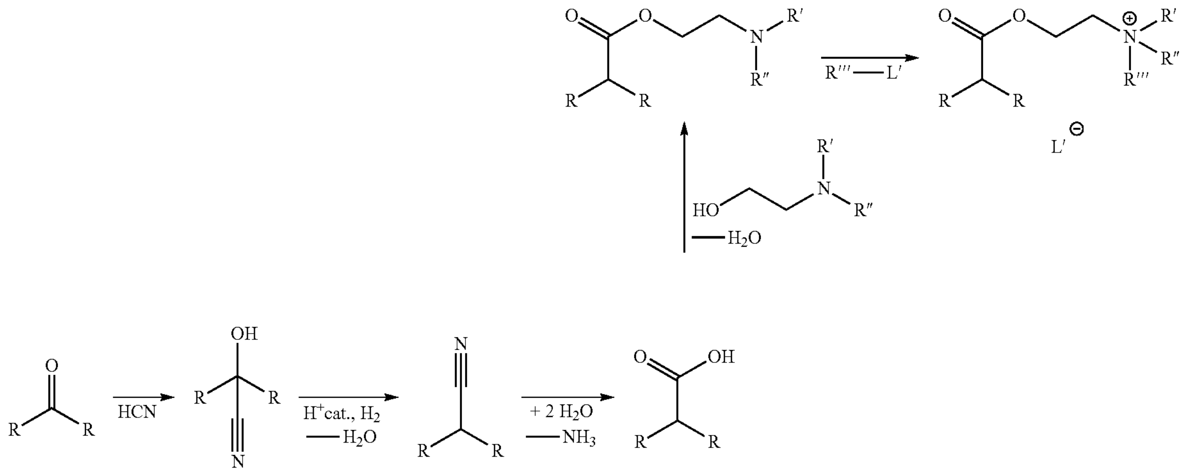

-continued

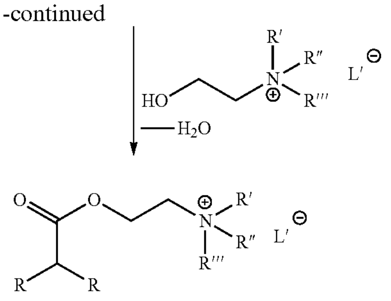

wherein L' is as defined hereinbefore.

As for the foregoing sequence of reactions, the individual reaction steps of this sequence have been described in the literature and are known to the skilled person. The skilled person will select suitable catalysts and reaction conditions based on his professional knowledge taking into account the desired target compound so that no further details need to be given here.

Synthesis of Compounds Wherein A is A-6 and J is J3

Compounds of this type may be obtained by a sequence of steps comprising the hydrogenation of an internal ketone to a secondary alcohol, followed by a carbonate interchange reaction involving dimethyl carbonate and the thus obtained secondary alcohol. Then a second carbonate interchange reaction with dimethylaminoethanol followed by quaternization yields the desired product.

In the first step, the hydrogenation of the internal ketone to the secondary alcohol can be carried out in an autoclave, preferably equipped with a stirring device (such as e.g. a Rushton turbine) without any added solvent. The internal ketone and a suitable catalyst (e.g. palladium metal on carbon) are introduced into the reactor which is thereafter sealed. Then the temperature is increased above the melting point of the ketone (temperature usually in the range from 80 to 120° C.) and the mixture is stirred. The reactor atmosphere is purged with nitrogen several times followed by purging the reactor with hydrogen. The temperature is then increased to appr. 120 to 180° C. (preferably appr. 150° C.). and the mixture is stirred at such elevated temperature maintaining superatmospheric hydrogen pressure (10 to 80 bar) until completion of the reaction.

At the end of the reaction, the mixture is allowed to cool down to a temperature slightly above the melting point of the alcohol, the pressure is released and the catalyst can be filtered to obtain the secondary alcohol.

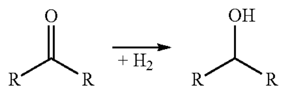

In the subsequent step, the secondary alcohol is carbonated to obtain a carbonate derivative. This step may be carried out e.g. in excess of a dialkylcarbonate $Alk^1$-O—C(═O)—O-$Alk^2$ wherein $Alk^1$ and $Alk^2$, which may the same or different, are an alkyl group having 1 to 8 carbon atoms, preferably an alkyl group having 1 to 4 carbon atoms which can act as the solvent with sodium methoxide (NaOMe) as the catalyst (generally used in amounts from 3 to 10 mol %, based on the amount of secondary alcohol). A preferred dialkylcarbonate is dimethylcarbonate (DMC) in which $Alk^1$ and $Alk^2$ are both methyl.

The reaction can be carried out by heating a mixture of the secondary alcohol in dialkylcarbonate in the presence of the catalyst at a temperature preferably between 50° C. and 250° C. The alcohol which is generated as the by-product during the reaction can be distilled out during the reaction.

At the end of the reaction the dialkyl carbonate can be evaporated and the residue can be engaged as such in a second trans-carbonation reaction with dialkylaminoethanol.

This reaction step is shown in the reaction scheme below:

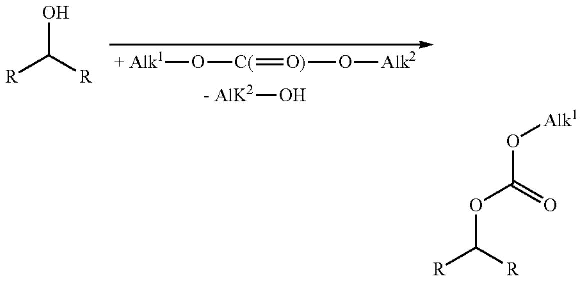

In the next step of the exemplary process, the secondary alcohol derived carbonate obtained as described above is reacted with a dialkylaminoethanol of formula HO—$CH_2$—$CH_2$—NR'R" (e.g. preferably dimethylaminoethanol, DMAE) according to the following reaction:

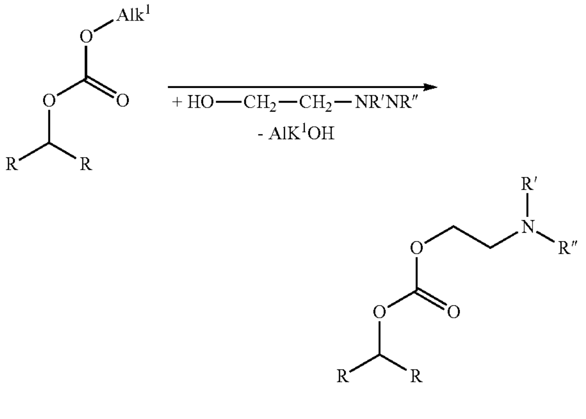

This second trans-carbonation can be conducted in a suitable solvent (e.g. toluene) using e.g. NaOMe as the catalyst (e.g. from previous step). The mixture of the starting asymmetrical alkyl sec-alkyl carbonate, dialkylaminoethanol and catalyst in toluene is generally heated to appr. 120° C. During the reaction the formed alcohol should be removed (e.g. through distillation). At the end of the reaction, the organic phase is usually washed with water to remove the catalyst and unreacted dialkylaminoethanol and the solvent is evaporated. The residue is re-dissolved in a suitable solvent (e.g. ethanol) in order to precipitate out the possibly formed fatty dialkyl carbonate. After filtration the product is obtained after solvent evaporation.

In the final step, the product obtained in the step described above is subjected to alkylation with e.g. an alkylating agent of general formula R'''-L'' wherein L'' is a monovalent anion or anionic group (such as e.g. methosulfate), preferably a dialkylsulfate, even more preferably dimethylsulfate (DMS), to obtain the desired quaternary ammonium derivative in accordance with the present invention:

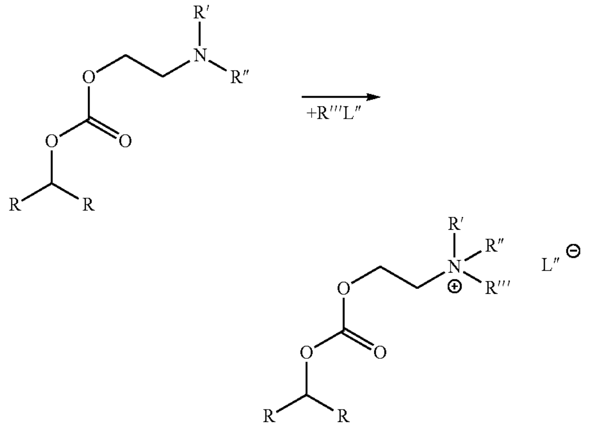

To 1 equivalent of dialkylsulfate (e.g. DMS) in a suitable solvent (e.g. methanol), a concentrated solution of carbonate-amine in the same solvent is progressively added under stirring at room temperature at a rate avoiding significant temperature increase due to reaction exothermy.

After the end of addition, the mixture is allowed to stir at room temperature (e.g. for one hour) and the volatiles (solvent) are removed under vacuum to afford the final product usually as a white wax.

The skilled person will select the appropriate reaction conditions and reactants for the process steps described hereinbefore based on his professional knowledge and taking into account the desired final product so that no details need to be given here.

Synthesis of Compounds Wherein A is A-3 or A-4, Exemplary Shown for Compounds of Formulae (V) or (VI)

In a first step, an internal ketone is subjected to a condensation reaction with a dialkylmalonate (e.g. dimethyl malonate) in the presence of a catalyst in an organic solvent at a temperature in the range of from 110 to 250° C., preferably from 125 to 175° C., even more preferably about 140° C. A suitable and preferred solvent for such reaction is xylene and a preferred catalyst is potassium tert-butoxide, the amount of which is usually in the range of from 2 to 10 mol %, preferably from 3 to 8 mol %, based on the molar quantity of the internal ketone.

The internal ketone (obtained e.g. as described in US 2018/093936), the dialkyl malonate (e.g. dimethyl malonate) and the catalyst are dissolved in the solvent (e.g. xylene) and reacted at elevated temperature (e.g. appr. 140° C.) for a period of time of usually from 1 to 72 hours. Water produced as by-product can be removed by azeotropic distillation. At the end of the reaction, the reaction medium is then usually cooled down to room temperature and the organic phase is washed with water in order to remove the catalyst.

The volatiles are then distilled out and the crude product is purified by re-dissolving the resulting oil in a suitable solvent (e.g. ethanol) allowing heavier by-products such as the ketone aldolisation/crotonisation adduct as well as the remaining starting ketone to precipitate. After filtration the filtrate can be evaporated (solvent removal) to afford the desired adduct.

The reaction scheme for this first step is given below:

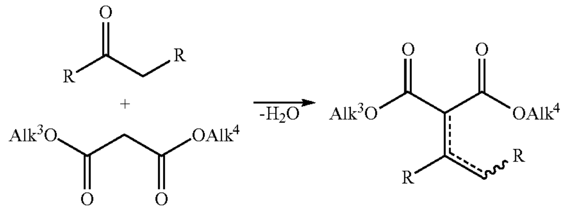

wherein $Alk^3$ and $Alk^4$, which may be the same or different, represent an alkyl group having 1 to 6 carbon atoms.

The product obtained in the first step can then be subjected to a transesterification with dialkylaminoethanol (e.g. dimethylaminoethanol). A suitable catalyst for this reaction step is dibutyltin oxide (usually in the amount of 2 to 10, preferably 3 to 8 mol % with respect to the malonate adduct obtained in the first step) and a suitable solvent is, as for the first step, xylene. The reaction temperature again is preferably in the range from 110 to 170° C. and even more preferably approximately 140° C.

The malonate adduct obtained in the first step is solubilized in the solvent (e.g. xylene), an excess of dialkylethanolamine (from 100% to 500% excess based on stoichiometry) is added to the solution, followed by the addition of the catalyst. The mixture is then allowed to stir at a temperature which is preferably in the range form 110° C. to 170° C., preferably appr. 140° C. and the formed alcohol is distilled out from the reaction medium. After completion of the reaction, the organic phase is washed with water in order to remove excess of dialkylaminoethanol and xylene is distilled out to afford the crude esteramine.

This second step can be represented by the following reaction scheme:

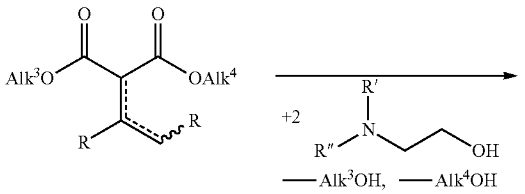

-continued

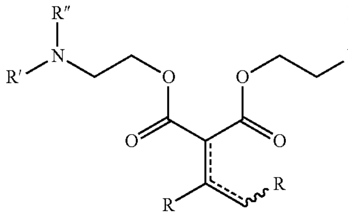

In a third step, the esteramine obtained in the second step can be alkylated with an alkylating agent of general formula R'''-L'' wherein L'' is a monovalent anion or anionic group (such as e.g. methosulfate), preferably a dialkylsulfate, even more preferably dimethylsulfate (DMS), to obtain the target quaternary ammonium compound of the present invention.

To a suitable amount of alkylating agent in a suitable solvent, a concentrated solution of esteramine in the same solvent is progressively added under stirring (usually at room temperature) at a rate avoiding significant temperature increase due to reaction exothermy.

After the end of the addition, the mixture is allowed to stir at room temperature (typically 15-30° C.) and the volatiles (mainly solvent and traces of alkylating agent (e.g. DMS)) are removed under vacuum to afford the final product as a white wax.

The reaction scheme for step 3 can be depicted as follows (with methanol as the solvent):

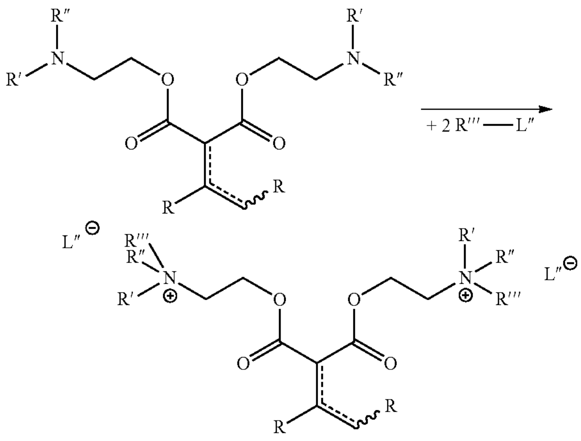

The wedged bond shown to the right is a representation of the fact that the reaction product is a mixture of three isomers derived from the structures in the reaction scheme of the first step.

The foregoing exemplary process will be suitably modified by the skilled person based on his professional knowledge to obtain other compounds of formula (V) and (VI). He will select the suitable reactants for reaction with the internal ketone and will modify the reaction conditions as necessary for other reactant/internal ketone combinations.

The skilled person will adopt the reaction conditions based on his professional knowledge and taking into account the desired target compound. The reaction steps as such have been described in the literature so that no further details need to be given here.

Synthesis of Compounds Wherein A is A-1 as Represented by Formula (VII)

In a first step of this exemplary process, an internal ketone is subjected to a reductive amination, e.g. with hydrogen and ammonia in accordance with the following reaction scheme:

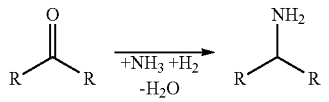

The reductive amination can be conducted in an autoclave using an excess of ammonia. The reactor is loaded with internal ketone, ethanol as the solvent (or another suitable solvent) and a suitable catalyst (e.g. Pt/C at a concentration of e.g. appr. 2 wt % with respect to the ketone substrate). The reactor atmosphere is purged several times with elevated pressure of nitrogen. Ammonia is then added into the reactor and then hydrogen and the temperature is increased to e.g. 120° C. while maintaining elevated pressure (e.g. 4 MPa) in the reactor. The reaction medium is stirred under those conditions until completion of the reaction.

Subsequently, the reaction product thus obtained is subjected to an alkylation in accordance with the following general scheme, shown for an alkyl chloroacetate as the alkylating agent:

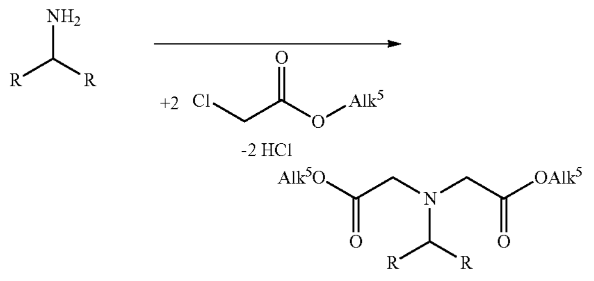

wherein $Alk^5$ is an alkyl group having 1 to 6 carbon atoms.

The reaction can be conducted using preferably an alkyl chloroacetate (particularly preferred methyl chloroacetate) as the alkylating agent either in a suitable solvent or using directly the alkyl chloroacetate as the solvent (meaning excess of reactant in comparison to sec-alkyl amine). A suitable base should be used during the reaction (e.g sodium carbonate) to neutralize formed HCl and a catalyst can be optionally employed (e.g. potassium iodide, KI) to speed up the reaction. The mixture is then allowed to stir at a temperature ranging from 50° C. to 250° C. until reaction completion. At the end of the reaction, the salts are filtered out and the organic phase can be washed with water. Then the volatiles can be removed under vacuum and the crude product is then engaged in the next steps.

The crude product thus obtained can then be subjected to a trans-esterification reaction with dialkylaminoethanol (e.g. dimethylaminoethanol (DMAE)), optionally in the presence of a suitable catalyst as described hereinbefore, according to the following reaction scheme:

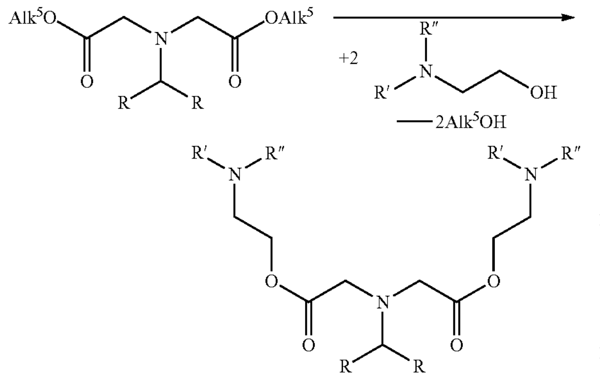

The reaction conditions can be chosen as described hereinbefore in the exemplary process for the synthesis of compounds wherein A is A-3 or A-4.

In the final step, the amine compound thus obtained is alkylated to obtain the desired compound in accordance with the present invention as shown for an alkylating agent R'''-L'' in the following reaction scheme:

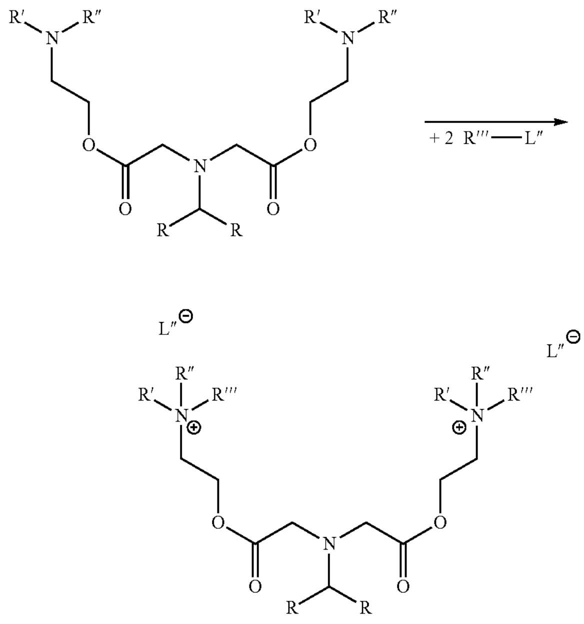

The same conditions as described hereinbefore for the methylation stage of compounds of formula (V) and (VI) can be employed.

Synthesis of Compounds Wherein A is Represented by A-5 as Exemplified by Formula (IX)

The respective compounds can preferably be obtained by two processes. The first process starts with a Piria ketonization followed by hydrogenation, dehydration, epoxydation+hydration and esterification. This is a multi-step process plugged on Piria technology but has the advantage of being salt-free and relying on chemical transformations which can be easily performed.

Ketonization

The basic reaction in the first step is:

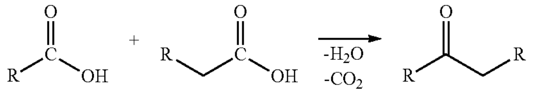

This reaction has been thoroughly described in U.S. patent Ser. No. 10/035,746, WO 2018/087179 and WO 2018/033607 to which reference is made for further details.

Hydrogenation

The internal ketone is then subjected to hydrogenation which can be carried out under standard conditions known to the skilled person for hydrogenation reactions:

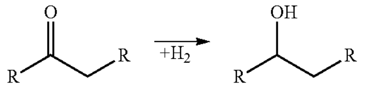

The hydrogenation reaction is conducted by contacting the internal ketone with hydrogen in an autoclave reactor at a temperature ranging from 15° C. to 300° C. and at a hydrogen pressure ranging from 1 bar to 100 bars. The reaction can be conducted in the presence of an optional solvent but the use of such solvent is not mandatory and the reaction can also be conducted without any added solvent. As examples of suitable solvents one can mention: methanol, ethanol, isopropanol, butanol, THF, methyl-THF, hydrocarbons, water or mixtures thereof. A suitable catalyst based on a transition metal should be employed for this reaction. As examples of suitable catalysts, one can mention heterogeneous transition metal based catalysts such as for example supported dispersed transition metal based catalysts or homogeneous organometallic complexes of transition metals. Examples of suitable transition metals are: Ni, Cu, Co, Fe, Pd, Rh, Ru, Pt, Ir. As examples of suitable catalysts one can mention Pd/C, Ru/C, $Pd/Al_2O_3$, Pt/C, $Pt/Al_2O_3$, Raney Nickel, Raney Cobalt etc. At the end of the reaction, the desired alcohol can be recovered after appropriate work-up. The skilled person is aware of representative techniques so no further details need to be given here. Details of this process step can e.g. be found in U.S. patent Ser. No. 10/035,746 to which reference is made here.

The skilled person will select suitable reaction conditions based on his professional experience and taking into account the specific target compound to be synthesized.

Accordingly, no further details need to be given here.

Dehydration

In the next step, the alcohol thus obtained is subjected to dehydration to obtain an internal olefin. This reaction can also be carried out under standard conditions known to the skilled person for respective dehydration reactions (e.g. U.S. patent Ser. No. 10/035,746, example 4) so that no further details need to be given here:

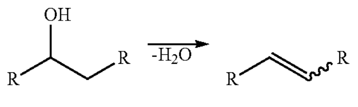

The dehydration reaction is conducted by heating the secondary alcohol in a reaction zone in the presence of a suitable catalyst at a temperature ranging between 100° C. and 400° C. The reaction can be conducted in the presence of an optional solvent but the use of such solvent is not mandatory and the reaction can also be conducted without any added solvent. As examples of solvents one can mention: hydrocarbons, toluene, xylene or their mixture. A catalyst must be employed for this reaction. Suitable examples of catalysts are acidic (Lewis or Bronsted) catalysts either heterogeneous solid acid catalysts or homogeneous catalysts. As examples of heterogeneous catalysts one can mention alumina ($Al_2O_3$), silica ($SiO_2$), aluminosilicates ($Al_2O_3$—$SiO_2$) such as zeolites, phosphoric acid supported on silica or alumina, acidic resins such as Amberlite® etc. Homogeneous catalysts can also be employed and one can mention the following suitable acids: $H_2SO_4$, HCl, trifluoromethanesulfonic acid, para-toluenesulfonic acid, $AlCl_3$, $FeCl_3$ etc. Water that is generated during the reaction can be distilled out from the reaction medium in the course of the reaction. At the end of the reaction, the desired olefin can be recovered after appropriate work-up. The skilled person is aware of representative techniques and same are e.g. described in U.S. patent Ser. No. 10/035,746 so that no further details need to be given here.

Epoxidation and Epoxide Hydration

This internal olefin can thereafter be oxidized to the respective diol wherein the double bond is substituted by two hydroxyl groups in accordance with the following scheme (where the reactants are just exemplary for respective groups of compounds serving the respective function):

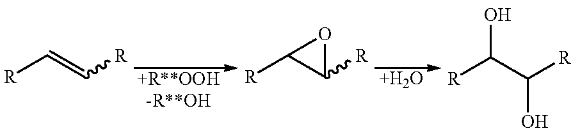

wherein R can be hydrogen or a hydrocarbon group that can be substituted and/or interrupted by a heteroatom or heteroatom containing groups, or R can be an acyl group of general formula R*—C(═O)—wherein R* can have the same meaning as R**.

The epoxidation reaction is conducted by contacting the internal olefin with an appropriate oxidizing agent in a reaction zone at a temperature ranging from 15° C. to 250° C. As suitable oxidizing agents one can mention peroxide compounds such as hydrogen peroxide ($H_2O_2$) that can be employed in the form of an aqueous solution, organic peroxides such as peracids of general formula R**—$CO_3H$ (for example meta-chloroperoxybenzoic acid, peracetic acid etc. . . . ) or alkyl hydroperoxides of general formula R*—$O_2H$ (for example cyclohexyl hydroperoxide, cumene hydroperoxide, tert-butyl hydroperoxide) where R** in the peracid or the alkyl hydroperoxide is a hydrocarbon group that can be substituted and/or interrupted by a heteroatom or heteroatoms-containing groups. The reaction can be conducted in the presence of an optional solvent but the use of such solvent is not mandatory and the reaction can also be conducted without any added solvent. As example of suitable solvents one can mention: $CHCl_3$, $CH_2Cl_2$, tert-butanol or their mixtures. In the case $H_2O_2$ is used as the oxidizing agent, the presence of an organic carboxylic acid during the reaction can be beneficial as it will generate in-situ a peracid compound by reaction with $H_2O_2$. As examples of suitable carboxylic acids one can mention: formic acid, acetic acid, propionic acid, butanoic acid, benzoic acid etc. A catalyst can also be used to promote the reaction. Suitable catalysts are Lewis or Bronsted acids and one can mention for example: perchloric acid ($HClO_4$), trifluoromethanesulfonic acid, heterogeneous titanium silicalite ($TiO_2$—$SiO_2$), heterogeneous acidic resins such as Amberlite®, homogeneous organometallic complexes of manganese, titanium, vanadium, rhenium, tungsten, polyoxometellates etc.

At the end of the reaction, the desired epoxide can be recovered after appropriate work-up and the skilled person is aware of representative techniques so that no further details need to be given here. The epoxide can be directly engaged in the hydration step without further purification.

The ring opening reaction can be performed by contacting the epoxide with water in the presence of a suitable catalyst at a temperature ranging from 15° C. to 150° C. As examples of catalysts one can mention Bronsted or Lewis acid catalysts such as: $H_2SO_4$, HCl, perchloric acid ($HClO_4$), trifluoromethanesulfonic acid, para-toluenesulfonic acid, heterogeneous acidic resins such as Amberlite® etc. The reaction can be conducted in the presence of an optional solvent to facilitate reagent contact and one can mention: Me-THF, THF, DMSO, tert-butanol, methanol, ethanol, isopropanol, acetonitrile, or their mixture. The reaction can also be conducted without any added solvent. At the end of the reaction, the desired diol can be recovered after appropriate work-up and the skilled person is aware of representative techniques so that no further details need to be given here.

Esterification and Amine Condensation

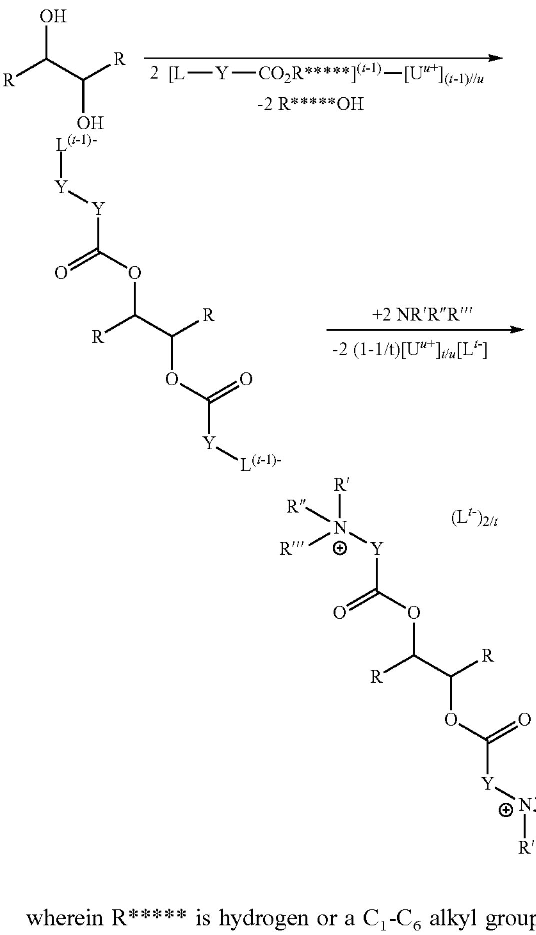

wherein R***** is hydrogen or a $C_1$-$C_6$ alkyl group.

The esterification is first performed by contacting the diol with a carboxylic acid or an ester of a carboxylic acid of general formula:

$$[L\text{-}Y—CO_2R^{*****}]^{(t-1)-}[U^{u+}]_{(t-1)/u}$$

wherein Y is a divalent hydrocarbon radical containing between 1 and 6 carbon atoms and L is a leaving group.

In the case the leaving group L already carries a negative charge in the carboxylic acid or ester reactant (this is the case when (t−1) is equal or superior to 1 or when t is equal or superior to 2), a cation noted $U^{u+}$ (with u preferably being 1, 2 or 3, even more preferably 1) must be present in the reactant to ensure the electroneutrality (in this case the cation possesses a $u^+$ charge). This cation may e.g. be selected from $H^+$, alkaline metal or alkaline earth metal cations (e.g. $Na^+$, $K^+$, $Ca^{2+}$), $Al^{3+}$ or ammonium, to mention only a few examples.

An example for a compound with t equal to 1 is the compound $CH_3—O—SO_3—CH_2—COOR^{***}$ which, for $R^{***}$ being H, yields the compound $CH_3—O—SO_3—CH_2—COOH$ which can be designated as 2-((methoxysulfonyl)oxy)acetic acid.

An example for t being equal to 2 is sodium carboxymethylsulfate acid in which $[L\text{-}Y—COOR^{***}]^{t-1-}[U^{u+}]_{(t-1/u)}$ is $[Na^+][O—SO_2—O—CH_2—COOR^{*}]^-$ with $R^{***}$ being H, U being Na and thus $[U^{u+}]_{t/u}[L^{t-}]$ being $Na_2SO_4$.

As further examples of compounds in which t is equal to 1 and thus no cation is present, one can mention: chloroacetic acid, bromoacetic acid and 2-chloropropionic acid.

The esterification can preferably be conducted at a temperature ranging from 50° C. to 250° C. in the presence of an optional solvent. However the presence of such solvent is not mandatory and the reaction can be also conducted without any added solvent. As example of suitable solvents one can mention: toluene, xylene, hydrocarbons, DMSO, Me-THF, THF or mixtures thereof. Water that is formed as a by-product during the reaction can be removed from the reaction medium by distillation over the course of the reaction. A catalyst can also be employed during the reaction and suitable catalysts are Bronsted or Lewis acid catalysts. As preferred examples of catalysts one can mention: $H_2SO_4$, para-toluenesulfonic acid, trifluoromethanesulfonic acid, HCl, or heterogeneous acidic resins such as Amberlite®, $AlCl_3$ etc. At the end of the reaction, the desired diester can be recovered after appropriate work-up and the skilled person is aware of representative techniques so that no further details need to be given here.

The amine condensation reaction is performed by contacting the intermediate diester obtained as described above with an amine of general formula NR'R"R"' where R', R" and R"' are $C_1$ to $C_4$ alkyl groups, preferably methyl or ethyl, most preferably methyl. The reaction can be conducted at a temperature ranging from 15° C. to 250° C. in the presence of a suitable solvent. As example of a suitable solvent one can mention: THF, Me-THF, methanol, ethanol, isopropanol, DMSO, toluene, xylene or their mixture. Alternatively the reaction can be also conducted in the absence of any added solvent. During this reaction, there is a nucleophilic attack of the amine that substitutes $L^{(t-1)-}$ in the diester, $L^{(t-1)-}$ plays the role of the leaving group. $L^{t-}$ becomes then the counter-anion of the final quaternary ammonium compound. In the case the leaving group already carries a negative charge in the diester reactant (this is the case when (t−1) is equal or superior to 1 or when t is equal or superior to 2) there is also formation of a salt as the by-product of the reaction (with the general chemical formula $[U^{u+}]_{t/u}[L^{t-}]$ as shown in the equation scheme above).

Acyloin Condensation

An alternative process for the synthesis of compounds in accordance with the present invention wherein A is represented by A-5 and shown in the scheme below for compounds of formula (IX) proceeds via an acyloin condensation in accordance with the following scheme:

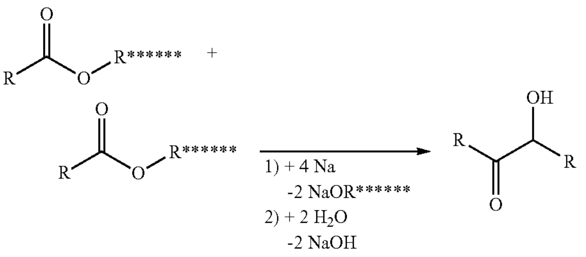

wherein $R^{******}$ is an alkyl group having from 1 to 6 carbon atoms.

The acyloin condensation is generally performed by reacting an ester (typically a fatty acid methyl ester) with sodium metal as the reducing agent. The reaction can be performed in a high boiling point aromatic solvent such as toluene or xylene where the metal can be dispersed at a temperature above its melting point (around 98° C. in the case of sodium). The reaction can be conducted at a temperature ranging from 100° C. to 200° C. At the end of the reduction, the reaction medium can be carefully quenched with water and the organic phase containing the desired acyloin product can be separated. The final product can be obtained after a proper work-up and the skilled person is aware of representative techniques so that no further details need to be given here.

Reactions of this type have been described in the literature, e.g. in Hansley, J. Am. Chem. Soc 1935, 57, 2303-2305 or van Heyningen, J. Am. Chem. Soc. 1952, 74, 4861-4864 or in Rongacli et al., Eur. J. Lipd Sci. Technol. 2008, 110, 846-852, to which reference is made herewith for further details.

Keto-Alcohol Hydrogenation

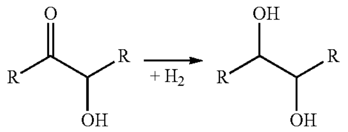

This reaction can be conducted using the conditions described hereinbefore for the first process variant for the manufacture of compounds of formula (IX), respectively compounds wherein A is represented by A-5.

The subsequent reaction steps are also as described hereinbefore for the first process variant for the manufacture of compounds of formula (IX), respectively compounds wherein A is represented by A-5.

A suitable process for the manufacture of compounds wherein A is represented by A-2, more specifically for compounds of formula (VIII) is described in the experimental part hereinafter.

The exemplary processes described before are examples of suitable processes, i.e. there might be other suitable processes to synthesize the compounds in accordance with the present invention. The processes described hereinbefore are thus not limiting as far as the methods of manufacture of the compounds according to the present invention is concerned.

The number of carbon atoms of the two groups R in compounds of formula IV, V, VII and VIII are preferably any of the following couples if the internal ketones used as reactant in the exemplary processes described hereinbefore are obtained from natural fatty acids having an even number of carbon atoms.

(5,5), (7,7), (9,9), (11,11), (13,13), (15,15), (17,17
(7,9), (7,11), (7,13), (7,15), (7,17)
(9,11), (9,13), (9,15), (9,17)
(11,13), (11,15), (11,17)
(13,15), (13,17)
(15,17)

If the internal ketone is derived from fatty acids comprising an odd number of carbon atoms, other couples are possible and will be obtained.

For compounds of formula VI and IX the number of carbon atoms of the two groups R are preferably any of the following couples if the internal ketones used as reactant in the exemplary processes described hereinbefore are derived from natural fatty acids having an even number of carbon atoms:

(4,5), (6,7), (8,9), (10,11), (12,13), (14,15), (16,17)
(7,8), (7,10), (7,12), (7,14), (7,16)
(9,10), (9,12), (9,14), (9,16)
(11,12), (11,14), (11,16)
(13,14), (13,16)
(15,16)

If the internal ketone is obtained from fatty acids comprising an odd numbers of carbon atoms, other couples are possible and will be obtained.

Compounds wherein A is represented by A-5 and in particular compounds of formula (IX) possess a particularly interesting and advantageous property profile of surfactant properties on one hand and biodegradability properties on the other hand. As biodegradability is becoming more and more an important aspect for surfactant products, compounds wherein A is represented by A-5, and in particular amongst this group the compounds of formula (IX), constitute a preferred embodiment of the present invention.

The compounds of the present invention can be used as surfactants. Surfactants are compounds that lower the surface tension (or interfacial tension) between two liquids, a liquid and a gas or between a liquid and a solid. Surfactants may act as detergents, wetting agents, emulsifiers, foaming agents, and dispersants.

Surfactants are usually organic compounds that are amphiphilic, meaning they contain both hydrophobic groups (their tails) and hydrophilic groups (their heads). Therefore, a surfactant contains both a water-insoluble (or oil-soluble) component and a water-soluble component. Surfactants will diffuse in water and adsorb at interfaces between air and water or at the interface between oil and water, in the case where water is mixed with oil. The water-insoluble hydrophobic group may extend out of the bulk water phase, into the air or into the oil phase, while the water-soluble head group remains in the water phase.

The adsorption of a cationic surfactant on negatively charged surfaces is an important property for such surfactants. This property is usually linked to the minimum concentration of surfactant needed to produce aggregation of a negatively charged cellulose nanocrystal (CNC, which is often used as reference material)) suspension in aqueous media. Consecutive variation of size can be monitored and followed by dynamic light scattering (DLS).

Following the protocol described in E. K. Oikonomou et al., "Fabric Softener-Cellulose Nanocrystal interaction: A Model for assessing Surface Deposition on Cotton", J. Phys. Chem. B, 2017, 121 (10), 2299-307 the adsorption properties of the quaternary ammonium compounds can be investigated by monitoring the ratio X=[surfactant]/[CNC]or the mass fraction M=[surfactant]/([surfactant+[CNC]), at fixed [surfactant]+[CNC]=0.01 wt % in aqueous solution, required to induce the agglomeration of the cellulose nanocrystals.

The biodegradability of the compounds of the present invention can be determined in accordance with procedures described in the prior art and known to the skilled person. Details about one such method, OECD standard 301, are given in the experimental section hereinafter.

Co-Softeners:

The fabric softeners of the present invention comprise a fatty co-softener. These are typically present at from 0.1 to 20% and particularly at from 0.4 to 15%, preferably 1 to 15% based on the total weight of the composition.

In the context of this invention a fatty cosoftener is considered to be a material comprising an aliphatic carbon chain. Preferably the carbon chain comprises more than 6 carbons, more preferably more than 8 carbons and preferably less than 30 carbons. The aliphatic chain may be saturated or unsaturated and my be branched or unbranched.

Preferred fatty co-softeners include fatty esters, fatty alcohols, fatty acids and combinations thereof. Fatty esters that may be employed include fatty monoesters, such as glycerol monostearate, fatty sugar esters and fatty acid mono-esters. Fatty acids which may be employed include hardened tallow fatty acid or hardened vegetable fatty acid (available under the trade name Pristerene™, ex Croda). Fatty alcohols which may be employed include tallow alcohol or vegetable alcohol, particularly preferred are hardened tallow alcohol or hardened vegetable alcohol (available under the trade names Stenol™ and Hydrenol™, ex BASF and Laurex™ CS, ex Huntsman).

Preferably the fatty co-softener has a fatty chain length of C12 to C22, preferably C14 to C20.

The weight ratio of the softening active to the fatty co-softening agent is preferably from 10:1 to 1:2, more preferably 5:1 to 1:2, most preferably 3:1 to 1:2, e.g. 2:1 to 1:1.

When used in combination with tri-ethanol amine quaternary ester quats, fatty co-softeners are known to reduce the softening levels, however when combined with the softening actives described, surprisingly a softening benefit is demonstrated.

Perfumes:

The fabric softener of the present invention preferably comprises 0.1 to 30 wt. % perfume materials, i.e. free perfume and/or perfume microcapsules. As is known in the art, free perfumes and perfume microcapsules provide the consumer with perfume hits at different points during the laundry process. It is particularly preferred that the fabric softeners of the present invention comprise a combination of both free perfume and perfume microcapsules.

Preferably the fabric softeners of the present invention comprises 0.1 to 20 w.t. % perfume materials, more preferably 0.5 to 15 w.t. % perfume materials, most preferably 1 to 10 w.t. % perfume materials.

Useful perfume components may include materials of both natural and synthetic origin. They include single compounds and mixtures. Specific examples of such components may be found in the current literature, e.g., in Fenaroli's Handbook of Flavor Ingredients, 1975, CRC Press; Synthetic Food Adjuncts, 1947 by M. B. Jacobs, edited by Van Nostrand; or Perfume and Flavor Chemicals by S. Arctander 1969, Montclair, N.J. (USA). These substances are well known to the person skilled in the art of perfuming, flavouring, and/or aromatizing consumer products.

Free Perfumes:

The fabric softeners of the present invention preferably comprise 0.1 to 15 wt. % free perfume, more preferably 0.5 to 8 wt. % free perfume.

Particularly preferred perfume components are blooming perfume components and substantive perfume components. Blooming perfume components are defined by a boiling point less than 250° C. and a Log P or greater than 2.5. Substantive perfume components are defined by a boiling point greater than 250° C. and a Log P greater than 2.5. Boiling point is measured at standard pressure (760 mm Hg). Preferably a perfume composition will comprise a mixture of blooming and substantive perfume components. The perfume composition may comprise other perfume components.

It is commonplace for a plurality of perfume components to be present in a free oil perfume composition. In the compositions for use in the present invention it is envisaged that there will be three or more, preferably four or more, more preferably five or more, most preferably six or more different perfume components. An upper limit of 300 perfume components may be applied.

Perfume Microcapsules:

The fabric softeners of the present invention preferably comprise 0.1 to 15 wt. % perfume microcapsules, more preferably 0.5 to 8 wt. % perfume microcapsules. The weight of microcapsules is of the material as supplied.

When perfume components are encapsulated, suitable encapsulating materials may comprise, but are not limited to; aminoplasts, proteins, polyurethanes, polyacrylates, polymethacrylates, polysaccharides, polyamides, polyolefins, gums, silicones, lipids, modified cellulose, polyphosphate, polystyrene, polyesters or combinations thereof. Particularly preferred materials are aminoplast microcapsules, such as melamine formaldehyde or urea formaldehyde microcapsules.

Perfume microcapsules of the present invention can be friable microcapsules and/or moisture activated microcapsules. By friable, it is meant that the perfume microcapsule will rupture when a force is exerted. By moisture activated, it is meant that the perfume is released in the presence of water. The fabric softeners of the present invention preferably comprise friable microcapsules. Moisture activated microcapsules may additionally be present. Examples of a microcapsules which can be friable include aminoplast microcapsules.

Perfume components contained in a microcapsule may comprise odiferous materials and/or pro-fragrance materials.

Particularly preferred perfume components contained in a microcapsule are blooming perfume components and substantive perfume components. Blooming perfume components are defined by a boiling point less than 250° C. and a Log P greater than 2.5. Preferably the encapsulated perfume compositions comprises at least 20 wt. % blooming perfume ingredients, more preferably at least 30 wt. % and most preferably at least 40 wt. % blooming perfume ingredients. Substantive perfume components are defined by a boiling point greater than 250° C. and a Log P greater than 2.5. Preferably the encapsulated perfume compositions comprises at least 10 wt. % substantive perfume ingredients, more preferably at least 20 wt. % and most preferably at least 30 wt. % substantive perfume ingredients. Boiling point is measured at standard pressure (760 mm Hg). Preferably a perfume composition will comprise a mixture of blooming and substantive perfume components. The perfume composition may comprise other perfume components.

It is commonplace for a plurality of perfume components to be present in a microcapsule. In the compositions for use in the present invention it is envisaged that there will be three or more, preferably four or more, more preferably five or more, most preferably six or more different perfume components in a microcapsule. An upper limit of 300 perfume components may be applied.

The microcapsules may comprise perfume components and a carrier for the perfume ingredients, such as zeolites or cyclodextrins.

Non-Ionic Surfactants:

The compositions may further comprise a nonionic surfactant. Typically these can be included for the purpose of stabilising the compositions. Suitable nonionic surfactants include addition products of ethylene oxide and/or propylene oxide with fatty alcohols, fatty acids and fatty amines. Any of the alkoxylated materials of the particular type described hereinafter can be used as the nonionic surfactant.

Suitable surfactants are substantially water soluble surfactants of the general formula (X):

$$R—Y—(C2H4O)z\text{-}CH2\text{-}CH2\text{-}OH \quad (X)$$

where R is selected from the group consisting of primary, secondary and branched chain alkyl and/or acyl hydrocarbyl groups; primary, secondary and branched chain alkenyl hydrocarbyl groups; and primary, secondary and branched chain alkenyl-substituted phenolic hydrocarbyl groups; the hydrocarbyl groups having a chain length of from 8 to about 25, preferably 10 to 20, e.g. 14 to 18 carbon atoms.

In the general formula for the ethoxylated nonionic surfactant, Y is typically:

$$—O—, —C(O)O—, —C(O)N(R)— \text{ or } —C(O)N(R)R—$$

in which R has the meaning given above for formula (X), or can be hydrogen; and Z is at least about 8, preferably at least about 10 or 11.

Preferably the nonionic surfactant has an HLB of from about 7 to about 20, more preferably from 10 to 18, e.g. 12 to 16. Genapol™ C200 (Clariant) based on coco chain and 20 EO groups is an example of a suitable nonionic surfactant.

If present, the nonionic surfactant is present in an amount from 0.01 to 10%, more preferably 0.1 to 5 by weight, based on the total weight of the composition.

A class of preferred non-ionic surfactants include addition products of ethylene oxide and/or propylene oxide with fatty alcohols, fatty acids and fatty amines. These are preferably selected from addition products of (a) an alkoxide selected from ethylene oxide, propylene oxide and mixtures thereof with (b) a fatty material selected from fatty alcohols, fatty acids and fatty amines.

Suitable surfactants are substantially water soluble surfactants of the general formula (XI):

$$R—Y—(C2H4O)z\text{-}CH2\text{-}CH2\text{-}OH \quad (XI)$$

where R is selected from the group consisting of primary, secondary and branched chain alkyl and/or acyl hydrocarbyl groups (when Y=—C(O)O, R≠an acyl hydrocarbyl group); primary, secondary and branched chain alkenyl hydrocarbyl groups; and primary, secondary and branched chain alkenyl-substituted phenolic hydrocarbyl groups; the hydrocarbyl groups having a chain length of from 10 to 60, preferably 10 to 25, e.g. 14 to 20 carbon atoms.

In the general formula for the ethoxylated nonionic surfactant, Y is typically:

—O—, —C(O)O—, —C(O)N(R)— or —C(O)N(R)R— in which R has the meaning given above for formula (XI), or can be hydrogen; and Z is at least about 6, preferably at least about 10 or 11.

Lutensol™ AT25 (BASF) based on C16:18 chain and 25 EO groups is an example of a suitable non-ionic surfactant. Other suitable surfactants include Renex 36 (Trideceth-6), ex Croda; Tergitol 15-S3, ex Dow Chemical Co.; Dihydrol LT7, ex Thai Ethoxylate ltd; Cremophor CO40, ex BASF and Neodol 91-8, ex Shell.

Cationic Polymer:

The compositions of the present invention may comprise a cationic polymer. This refers to polymers having an overall positive charge.

The cationic polymer may be naturally derived or synthetic. Examples of suitable cationic polymers include: acrylate polymers, cationic amino resins, cationic urea resins, and cationic polysaccharides, including: cationic celluloses, cationic guars and cationic starches.

The cationic polymer of the present invention may be categorised as a polysaccharide-based cationic polymer or non-polysaccharide based cationic polymers.

Polysaccharide based cationic polymers include cationic celluloses, cationic guars and cationic starches. Polysaccharides are polymers made up from monosaccharide monomers joined together by glycosidic bonds.

The cationic polysaccharide-based polymers present in the compositions of the invention have a modified polysaccharide backbone, modified in that additional chemical groups have been reacted with some of the free hydroxyl groups of the polysaccharide backbone to give an overall positive charge to the modified cellulosic monomer unit.

A preferred polysaccharide polymer is cationic cellulose. This refers to polymers having a cellulose backbone and an overall positive charge.

Cellulose is a polysaccharide with glucose as its monomer, specifically it is a straight chain polymer of D-glucopyranose units linked via beta-1,4 glycosidic bonds and is a linear, non-branched polymer.

The cationic cellulose-based polymers of the present invention have a modified cellulose backbone, modified in that additional chemical groups have been reacted with some of the free hydroxyl groups of the polysaccharide backbone to give an overall positive charge to the modified cellulose monomer unit.

A preferred class of cationic cellulose polymers suitable for this invention are those that have a cellulose backbone modified to incorporate a quaternary ammonium salt.

Preferably the quaternary ammonium salt is linked to the cellulose backbone by a hydroxyethyl or hydroxypropyl group. Preferably the charged nitrogen of the quaternary ammonium salt has one or more alkyl group substituents.

Example cationic cellulose polymers are salts of hydroxyethyl cellulose reacted with trimethyl ammonium substituted epoxide, referred to in the field under the International Nomenclature for Cosmetic Ingredients as Polyquaternium 10 and is commercially available from the Amerchol Corporation, a subsidiary of The Dow Chemical Company, marketed as the Polymer LR, JR, and KG series of polymers. Other suitable types of cationic celluloses include the polymeric quaternary ammonium salts of hydroxyethyl cellulose reacted with lauryl dimethyl ammonium-substituted epoxide referred to in the field under the International Nomenclature for Cosmetic Ingredients as Polyquaternium 24. These materials are available from Amerchol Corporation marketed as Polymer LM-200.

Typical examples of preferred cationic cellulosic polymers include cocodimethylammonium hydroxypropyl oxyethyl cellulose, lauryldimethylammonium hydroxypropyl oxyethyl cellulose, stearyldimethylammonium hydroxypropyl oxyethyl cellulose, and stearyldimethylammonium hydroxyethyl cellulose; cellulose 2-hydroxyethyl 2-hydroxy 3-(trimethyl ammonio) propyl ether salt, polyquaternium-4, polyquaternium-10, polyquaternium-24 and polyquaternium-67 or mixtures thereof.

More preferably the cationic cellulosic polymer is a quaternised hydroxy ether cellulose cationic polymer. These are commonly known as polyquaternium-10. Suitable commercial cationic cellulosic polymer products for use according to the present invention are marketed by the Amerchol Corporation under the trade name UCARE.

The counterion of the cationic polymer is freely chosen from the halides: chloride, bromide, and iodide; or from hydroxide, phosphate, sulphate, hydrosulphate, ethyl sulphate, methyl sulphate, formate, and acetate.

A non-polysaccharide-based cationic polymer is comprised of structural units, these structural units may be non-ionic, cationic, anionic or mixtures thereof. The polymer may comprise non-cationic structural units, but the polymer must have a net cationic charge. The cationic polymer may consists of only one type of structural unit, i.e., the polymer is a homopolymer. The cationic polymer may consists of two types of structural units, i.e., the polymer is a copolymer. The cationic polymer may consists of three types of structural units, i.e., the polymer is a terpolymer. The cationic polymer may comprises two or more types of structural units. The structural units may be described as first structural units, second structural units, third structural units, etc. The structural units, or monomers, may be incorporated in the cationic polymer in a random format or in a block format. The cationic polymer may comprise a nonionic structural units derived from monomers selected from: (meth)acrylamide, vinyl formamide, N, N-dialkyl acrylamide, N, N-dialkylmethacrylamide, C1-C12 alkyl acrylate, C1-C12 hydroxyalkyl acrylate, polyalkylene glycol acrylate, C1-C12 alkyl methacrylate, C1-C12 hydroxyalkyl methacrylate, polyalkylene glycol methacrylate, vinyl acetate, vinyl alcohol, vinyl formamide, vinyl acetamide, vinyl alkyl ether, vinyl pyridine, vinyl pyrrolidone, vinyl imidazole, vinyl caprolactam, and mixtures thereof.

The cationic polymer may comprise a cationic structural units derived from monomers selected from: N, N-dialkylaminoalkyl methacrylate, N, N-dialkylaminoalkyl acrylate, N, N-dialkylaminoalkyl acrylamide, N, N-dialkylaminoalkylmethacrylamide, methacylamidoalkyl trialkylammonium salts, acrylamidoalkylltrialkylamminium salts, vinylamine, vinylimine, vinyl imidazole, quaternized vinyl imidazole, diallyl dialkyl ammonium salts, and mixtures thereof.

Preferably, the cationic monomer is selected from: diallyl dimethyl ammonium salts (DADMAS), N, N-dimethyl aminoethyl acrylate, N,N-dimethyl aminoethyl methacrylate (DMAM), [2-(methacryloylamino)ethyl]trl-methylammonium salts, N, N-dimethylaminopropyl acrylamide (DMAPA), N, N-dimethylaminopropyl methacrylamide (DMAPMA), acrylamidopropyl trimethyl ammonium salts (APTAS), methacrylamidopropyl trimethylammonium salts (MAPTAS), quaternized vinylimidazole (QVi), and mixtures thereof.

The cationic polymer may comprise a anionic structural units derived from monomers selected from: acrylic acid (AA), methacrylic acid, maleic acid, vinyl sulfonic acid, styrene sulfonic acid, acrylamidopropylmethane sulfonic acid (AMPS) and their salts, and mixtures thereof.

Some cationic polymers disclosed herein will require stabilisers i.e. materials which will exhibit a yield stress in the ancillary laundry composition of the present invention. Such stabilisers may be selected from: thread like structuring systems for example hydrogenated castor oil or trihydroxystearin e.g. Thixcin ex. Elementis Specialties, cross-linked polyacrylic acid for example Carbopol ex. Lubrizol and gums for example carrageenan.

Preferably the cationic polymer is selected from; cationic polysaccharides and acrylate polymers. More preferably the cationic polymer is a cationic acrylate polymer.

The molecular weight of the cationic polymer is preferably greater than 20 000 g/mol, more preferably greater than 25 000 g/mol. The molecular weight is preferably less than 2 000 000 g/mol, more preferably less than 1 000 000 g/mol.

Fabric softeners according to the current invention preferably comprise cationic polymer at a level of 0.1 to 10 wt. % of the formulation, preferably 0.25 to 7.5 wt. % of the formulation, more preferably 0.35 to 5 wt. % of the formulation.

The compositions may comprise other ingredients of fabric softener liquids as will be known to the person skilled in the art. Among such materials there may be mentioned: antifoams, insect repellents, shading or hueing dyes, preservatives (e.g. bactericides), pH buffering agents, perfume carriers, hydrotropes, anti-redeposition agents, soil-release agents, polyelectrolytes, anti-shrinking agents, anti-wrinkle agents, anti-oxidants, dyes, colorants, sunscreens, anti-corrosion agents, drape imparting agents, anti-static agents, sequestrants and ironing aids. The products of the invention may contain pearlisers and/or opacifiers. A preferred sequestrant is HEDP, an abbreviation for Etidronic acid or 1-hydroxyethane 1,1-diphosphonic acid.

In one aspect of the present invention, fabric is washed with the fabric softener compositions described herein. The treatment is preferably during the washing process. This may be hand washing or machine washing. Preferable the fabric softener is used in the rinse stage of the washing process.

Preferably the fabric are treated with a 10 to 100 ml dose of fabric softener for a 3 to 7 kg load of clothes. More preferably, 10 to 80 ml for a 3 to 7 kg load of clothes.

In one aspect of the present invention is a method of softening fabric, wherein the fabric is contacted with the fabric softeners as described herein in the rinse stage of the washing process.

In one aspect of the present invention is the use of the fabric softeners as described herein to soften fabric.

1. A fabric softener composition comprising:

a. 1 to 20 wt. % ionic compound of general formula I:

(I)

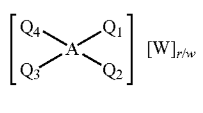

wherein

A is a tetravalent linker selected from the group consisting of A-1 to A-6

A-1

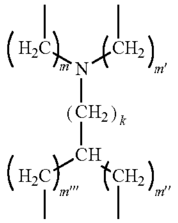

A-2

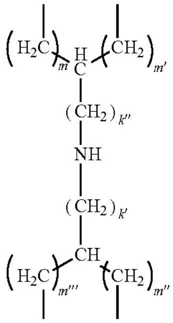

A-3

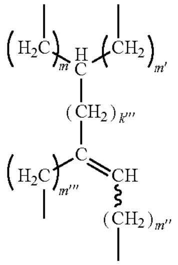

A-4

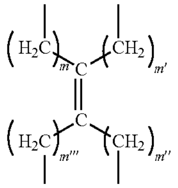

A-5

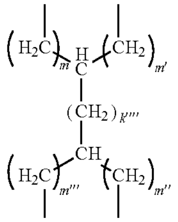

A-6

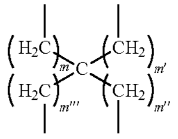

$Q_1$ to $Q_4$, which may be identical or different from each other, are selected from the group consisting of hydrogen, R and X, and W is an anion or an anionic group bearing w negative charges and r is the number of substituents Q1 to Q4 which are represented by a group X, wherein R, which may be the same or different at each occurrence, is a C5-C27 aliphatic group, m, m' m" and m", which may be the same or different at each occurrence, are 0, 1, 2 or 3.

k, k'k", k'" and k", which may be the same or different, are 0, 1, 2 or 3, and X, which may be the same or different at each occurrence, is represented by formula II (II)

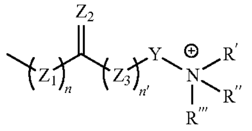

wherein $Z_1$, $Z_2$ and $Z_3$, which may be the same or different, are O, S or NH Y is a divalent C1-Ce aliphatic radical, R', R" and R", which may be the same or different, are hydrogen or a $C_1$ to $C_4$ alkyl group, n and n' are 0 or 1 with the sum of n+n' being 1 or 2, wherein at least one of $Q_1$ to $Q_4$ is represented by X and at least two of groups $Q_1$ to $Q_4$ are represented by R, which groups R may be the same or different at each occurrence, and wherein, if the ionic compound is such that (i) A is represented by A-6 with m, m', m" and m'" equal to 0, (ii) one and only one of $Q_1$ to $Q_4$ is represented by a substituent X and n in the substituent X is equal to 0 and (iii) two and only two of $Q_1$ to $Q_4$ are represented by substituents R, then the difference of the number of carbon atoms of the two substituents R is 0, 1, 3 or more than 3.

b. 0.1 to 20 wt. % fatty co-softener; and c. Water.

2. A fabric softener composition according to claim 1 wherein the ionic compound comprises one or two groups X and two and only two groups R.

3. A fabric softener composition according to claim 1 or 2 wherein n+n' of the ionic compound is 1.

4. A fabric softener composition according to claim 1 or 2 wherein n+n' of the ionic compound is 2.

5. A fabric softener composition according to any preceding claim wherein the n' of the ionic compound is 1 and the Y of the ionic compound is a $C_2$-$C_6$ aliphatic group.

6. A fabric softener composition according to any preceeding claim wherein of substituents $Z_1$, $Z_2$ and $Z_3$ at least one is oxygen, more preferably at least two and most preferably all three of substituents $Z_1$, $Z_2$ and $Z_3$ are oxygen.

7. A fabric softener composition according to any preceding claims 1 to 4 wherein the A of the ionic compound is represented by A-6, m, m', m" and m'" are 0, $Z_1$ to $Z_3$ are O and wherein the ionic compound comprises two groups R and one group X.

8. A fabric softener composition according to claim 7 wherein the n of the ionic compound is 0 and the n' of the ionic compound is 1 or wherein the n of the ionic compound is 1.

9. A fabric softener composition according to any of claims 1 to 5 wherein the A of the ionic compound is represented by A-3 or A-4, m, m', m", m'" and k'" are 0 and two of substituents $Q_1$ to $Q_4$ are represented by groups X with both X attached to the same carbon atom of linker A and two groups R attached to the same or to different carbon atoms of linker A.

10. A fabric softener composition according to any of claims 1 to 5 wherein the A of the ionic compound represented by A-1, m and m' are 1, m" and m'" are 0, k is 0 and two substituents $Q_1$ to $Q_4$ are represented by groups X with both groups X being attached to the nitrogen atom of linker A.

11. A fabric softener composition according to any of claims 1 to 5 wherein the A of the ionic compound represented by A-2, k' is 0, k" is 1, m is 1, m', m" and m'" are 0 and two of substituents $Q_1$ to $Q_4$ are represented by groups X attached to the same carbon atom of linker A.

12. A fabric softener composition according to any of claims 1 to 5 wherein the A of the ionic compound represented by A-5, m, m', m" m'" and k"" are 0, two of substituents $Q_1$ to $Q_4$ are X with each carbon atom of linker A carrying one group X and one group R wherein X and R might be the same or different at each occurrence.

13. A fabric softener composition according to claim 12 wherein in the groups X, n is 1, n' is 0, and Y of the ionic compound are $CH_2$.

14. A fabric softener composition according to any preceding claim, wherein the fatty co-softener is selected from fatty esters, fatty acids, fatty alcohols and combinations thereof.

15. Use of a fabric softener formulation according to any preceding claim, to soften fabrics.

EXAMPLES

Example 1—Synthesis of a Quaternary Ammonium Compound of Formula IV Wherein J is J3, i.e. Wherein n and n' in Group X are Each 1, Starting from 12-Tricosanol $C_{23}$ 12-tricosanol was obtained from $C_{23}$ 12-tricosanone through catalytic hydrogenation according to US-A 2018/093936 (see example 3 in this document).

All the reactions were conducted in carefully dried vessels and under an inert argon atmosphere.

Fresh commercial anhydrous $CHCl_3$ (amylene stabilized), anhydrous toluene and anhydrous acetonitrile were used as such. Choline chloride (which is hygroscopic) was washed several times with anhydrous THF and dried under vacuum prior to use.

Into a 500 mL round bottom flask equipped with a condenser, a temperature probe, a heater and a magnetic stirrer were added 38.37 g of 12-tricosanol (112.7 mmol) followed by 150 mL of toluene. The mixture was then allowed to stir at room temperature and 0.1 g of solid KOH (1.7 mmol, 1.6 mol %) was then added followed by 18.26 g of carbonyldiimidazole (112.7 mmol, 1 eq.) and an additional 20 mL of toluene.

The mixture was then allowed to stir at 70° C.; at this temperature the mixture became transparent. Reaction progress was followed by $^1$H-NMR and after three hours at 70° C., an alcohol conversion of 99% was reached.

All the volatiles were then removed through distillation at 50° C., 9 mbar to afford 59.4 g of a residue which was used in the next stage without purification.

The residue was then solubilized in a mixture of 40 mL $CHCl_3$ and 40 mL of acetonitrile and 15.74 g of choline chloride (112.7 mmol, 1 eq.) was added at room temperature. The mixture was then allowed to stir at 50° C. overnight.

Over the course of the reaction, the reaction medium turned homogeneous and green. The reaction progress was followed by $^1$H-NMR and a conversion of 89% was obtained at this stage. The solvent was then removed under vacuum to afford around 79.1 g of crude.

The crude residue was purified by chromatography on silica gel (330 g of silica) in order to remove impurities and imidazole by-product (the specification is <0.5 wt % of imidazole) using an ethylacetate/methanol (AcOEt/MeOH) eluent (going from 100% AcOEt to 50:50 AcOEt:MeOH).

Five fractions were collected: the first fraction corresponding to the intermediate imidazole carbonate as well as the second fraction corresponding to the imidazole were discarded and the three remaining fractions were collected and re-purified.

For the second chromatography on silica gel, 200 g of silica was used with the same eluent system. Two fractions were collected: the first one was a mixture of product and imidazole and the second one was the pure product.

Finally the first fraction was purified again using 30 g of silica gel and the same eluent system to afford additional amount of product.

All clean fractions were collected affording 39.8 g of product as a white wax corresponding to 70% isolated yield.

$^1$H NMR ($CDCl_3$, 400 MHz) δ (ppm): 4.65 (quint, 1H), 4.61-4.51 (m, 2H), 4.22-4.02 (m, 2H), 3.52 (s, 9H), 1.61-1.44 (m, 4H), 1.32-1.12 (m, 36H), 0.84 (t, J=8.0 Hz, 6H).

$^{13}$C NMR ($CDCl_3$, 101 MHz) δ (ppm): 154.21, 80.88, 64.92, 61.24, 54.59, 33.96, 32.10, 29.83, 29.82, 29.80, 29.70, 29.68, 29.54, 25.36, 22.88, 14.31 (terminal $CH_3$).

Example 2—Synthesis of a Quaternary Ammonium Compound of Formula IV Wherein J is J3, i.e. Wherein n and n' in Group X are Each 1, Starting from 16-Hentriacontanol $C_{31}$ 16-hentriacontanol was obtained from $C_{31}$ 16-hentriacontanol through catalytic hydrogenation according to US-A US2018/093936 (see example 3 in this document).

All the reactions were conducted in carefully dried vessels and under an inert argon atmosphere.

Fresh commercial anhydrous $CHCl_3$ (amylene stabilized), anhydrous toluene and anhydrous acetonitrile were used as such. Choline chloride (which is hygroscopic) was washed several times with anhydrous THF and dried under vacuum prior to use.

In a 500 mL round bottom flask equipped with a condenser, a temperature probe, a heater and a magnetic stirrer were added 45.2 g of 16-hentriacontanol (99.9 mmol) followed by 150 mL of toluene. The mixture was then allowed to stir at room temperature and 0.1 g of solid KOH (1.7 mmol, 1.7 mol %) was then added followed by 17.0 g of carbonyldiimidazole (105 mmol, 1.05 eq.) and an additional 50 mL of toluene.

The mixture was then allowed to stir at 60° C.; at this temperature the mixture became transparent. Reaction progress was followed by $^1$H-NMR and after one hour at 60° C., an alcohol conversion >99% was reached.

All the volatiles were then removed through vacuum to afford a white residue which was used in the next stage without purification.

The residue was then solubilized in a mixture of 80 mL $CHCl_3$ and 80 mL of acetonitrile and 13.95 g of choline chloride (99.9 mmol, 1 eq.) was added at room temperature. The mixture was then allowed to stir at 55° C. overnight.

The reaction progress was followed by $^1$H-NMR and only a weak conversion of 30% was obtained at this stage. This weak conversion could be explained by KOH decomposition (for example by reaction with $CHCl_3$).

0.3 g of KOH (5.1 mmol) was then added and the mixture was stirred at reflux during an additional 3 hours. The conversion level reached 78% according to NMR.

An additional 0.2 g of KOH was again added followed by stirring at reflux during twelve hours.

At this stage, conversion level was 83% and the color of the mixture was brown.

The solvent was then removed under vacuum to afford around 84 g of crude.

The crude residue was purified by chromatography on silica gel (2 columns with 330 g of silica) in order to remove impurities and imidazole by-product (the specification is <0.5 wt % of imidazole) using an AcOEt/MeOH eluent (going from 100% AcOEt to 50:50 AcOEt:MeOH).

Four fractions were collected: the first fraction corresponded to the intermediate imidazole carbonate and the second fraction corresponded to the imidazole. The third fraction contained a mixture of imidazole and desired product and the last fraction corresponded to the desired product.

The fourth fractions of each column were collected and subjected to a second chromatography on silica gel. 330 g of silica was used with the same eluent system to afford the desired product with good purity. 36.6 g of product as a white wax was obtained corresponding to 60% isolated yield.

$^1$H NMR ($CDCl_3$, 400 MHz) δ (ppm): 4.66 (quint, 1H), 4.62-4.52 (m, 2H), 4.24-4.04 (m, 2H), 3.53 (s, 9H), 1.62-1.46 (m, 4H), 1.34-1.14 (m, 52H), 0.85 (t, J=6.8 Hz, 6H).

$^{13}$C NMR ($CDCl_3$, 101 MHz) δ (ppm): 154.20, 80.87, 64.91, 61.23, 54.58, 33.96, 32.11, 29.90, 29.85, 29.82, 29.72, 29.69, 29.55, 25.36, 22.88, 14.31 (terminal CH3).

Example 3—Synthesis of a Mixture of Quaternary Ammonium Compounds Wherein A is Represented by A-2 or A-3 (a Mixture of Compounds of Formula (V) and (VI)) Starting from $C_{31}$-16-Hentriacontanone Knoevenagel Condensation to Afford Diester Intermediate:

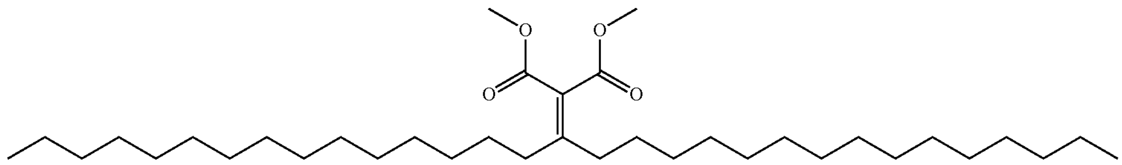 [SMILES: CCCCCCCCCCCCCCCC(CCCCCCCCCCCCCCC)=C(C(=O)OC)C(=O)OC]

All the reactions were conducted in carefully dried vessels and under an inert argon atmosphere.

Fresh commercial anhydrous $CHCl_3$, anhydrous THF and anhydrous pyridine were used as such.

In a 1 L double-jacketed reactor equipped with a mechanical stirrer (propeller with four inclined plows), a condenser, an addition funnel and a temperature probe were added 36.5 mL of $TiCl_4$ (63.00 g, 0.332 mole), followed by 146.3 mL of $CHCl_3$.

The mixture was stirred at −10° C. and anhydrous THF (358 mL) was slowly added through the addition funnel at a rate avoiding a temperature increase of the reaction medium above +5° C. During THF addition, a yellow precipitate appeared. Then 15.3 mL of dimethyl malonate (17.69 g, 0.134 mole) were added into the reaction mixture which was then allowed to stir at room temperature for 1 hour in order to allow malonate complexation to occur.

Then the mixture was allowed to cool down to 0° C. and a solution of 71.80 mL of anhydrous pyridine (70.50 g, 0.891 mole) in 23 mL of THF was slowly added into the reactor. During addition, the colour of the mixture turned red. The mixture was then allowed to stir at room temperature during 20 minutes to allow deprotonation to occur.

Finally, 50.00 g of $C_{31}$ ketone (0.111 mole) was added into the reaction mixture which was allowed to stir at room temperature during one night and during one more day at 35° C. 250 mL of water were then carefully added into the reactor followed by 250 mL of diethyl ether. The organic phase was separated and washed 4 times with 250 mL of water and one time with 200 mL of a saturated aqueous NaCl solution in order to remove pyridinium salts. The aqueous phases were combined and re-extracted with 3 times 250 mL of diethyl ether. The final organic phase was dried over $MgSO_4$, filtered and evaporated under vacuum to afford 70.08 g of crude orange oil. At this stage the crude contains residual amount of starting ketone as well as a main impurity corresponding to the condensation (aldolisation+crotonisation) of 2 equivalents of ketone.

The product could be easily purified by dissolving the oil in ethanol (the by-product and the starting ketone being not soluble in ethanol) followed by a filtration over celite.

The filtrate was evaporated, re-dissolved in $CHCl_3$, filtered again and evaporated to afford 52.57 g of oil with 95% of purity (RMN).

The overall purified yield was 79%.

$^1$H NMR ($CDCl_3$, 400 MHz) δ (ppm): 3.68 (s, 6H), 2.32-2.19 (m, 4H), 1.45-1.39 (m, 4H), 1.30-1.10 (m, 48H), 0.81 (t, J=6.4 Hz, 6H).

$^{13}$C NMR ($CDCl_3$, 101 MHz) δ (ppm): 166.30, 164.47, 123.65, 52.15, 34.61, 32.15, 30.16, 29.92, 29.91, 29.87, 29.76, 29.60, 28.65, 22.92, 14.34 (terminal CH3).

Transesterification with Dimethylaminoethanol to Afford Diamine Mixtures Intermediates:

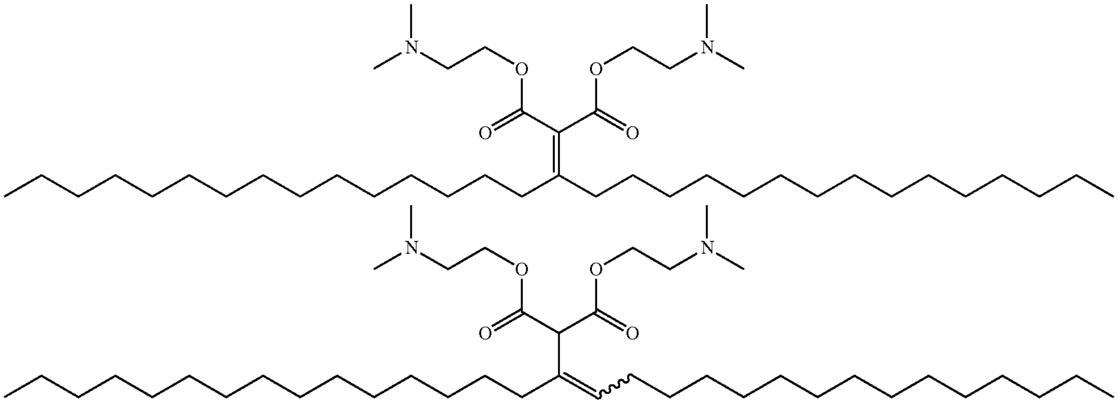

All the reactions were conducted in carefully dried vessels and under an inert argon atmosphere.

Fresh commercial anhydrous toluene and dimethylaminoethanol were used as such. In a 2 L double-jacketed reactor equipped with a mechanical stirrer (propeller with four inclined plows), a condenser with a distillation apparatus and a temperature probe were added 42.7 g of the internal ketone/dimethyl malonate adduct (75.6 mmol) followed by 50 mL of toluene. The mixture was stirred at room temperature and 30.4 mL of dimethylaminoethanol (26.9 g, 302.2 mmol, 4 eq.) was added to the reaction system followed by 50 mL of toluene. Then 0.9 g of the catalyst dibutyltin oxide (3.8 mmol, 5 mol %) was added to the reaction mixture followed by 200 mL of toluene.

Then the mixture was allowed to stir at 120° C. and the reaction progress was followed by NMR analysis. To run a proper analysis an aliquot of the reaction medium was sampled and diluted in diethyl ether, quenched with water, decanted and the organic phase was evaporated under vacuum to be analysed in $CDCl_3$ NMR solvent. After 4 days of stirring at 120° C. NMR analysis showed that the conversion level was around 83% with 91% selectivity. In addition, by-product methanol was also present in the distillation flask. The reaction mixture was then allowed to cool down at room temperature and quenched with 500 mL of water. The medium was decanted and the aqueous phase was extracted with three times of 500 mL of diethyl ether. The organic phases were collected and washed three times with 500 mL of water and one time with 500 mL of a saturated aqueous NaCl solution in order to remove excess of dimethylaminoethanol. The organic phase was then dried over MgSO4, filtered and evaporated to give 47.9 g of a crude dark oil. At this stage the crude contained a residual amount of the starting malonate.

The product was then purified by flash chromatography on silica gel with a first eluent consisting on $CHCl_3$/AcOEt mixture going through a gradient from 100% $CHCl_3$ to 100% AcOEt.

In order to remove all the product from the column, the column was also flushed with isopropanol+$NEt_3$ mixture (10% vol $NEt_3$) allowing getting additional pure product.

The clean fractions were collected affording, after solvent evaporation, 27.8 g of a pure product corresponding to 54% isolated yield.

NMR analysis showed that the product was in the form of a mixture of two position isomers with the following ratio: 54 mol % of the isomerized product (cis and trans diastereoisomers) and 46 mol % of methylenated product.

$^{1}H$ NMR ($CDCl_3$, 400 MHz) δ (ppm): 5.45-5.13 (m, 1H: isomer 2 cis+trans), 4.42 (s, 1H, isomer 2 cis or trans), 4.24-4.06 (m, 4H, isomer 1+2), 3.99 (s, 1H, isomer 2 cis or trans), 2.58-2.40 (m, 4H, isomer 1+2), 2.32-2.24 (m, 4H, isomer 1), 2.20 (s, 12H, isomer 1), 2.19 (s, 12H, isomer 2), 2.09-1.89 (m, 4H, isomer 2 cis+trans), 1.45-0.99 (m, 51H, isomer 1+2), 0.81 (t, J=6.8 Hz, 6H).

$^{13}C$ NMR ($CDCl_3$, 101 MHz) δ (ppm): 168.60, 168.41, 165.49, 164.05, 132.07, 131.57, 131.12, 130.77, 123.73, 63.35, 62.76, 58.08, 57.49, 57.45, 53.45, 45.73, 34.45, 30.07, 30.03, 29.72, 29.68, 29.58, 29.53, 29.45, 29.38, 28.46, 28.43, 28.27, 28.09, 22.70, 14.13 (terminal $CH_3$).

Methylation to Afford a Mixture of Compounds (V) and (VI):

All the reactions were conducted in carefully dried vessels and under an inert argon atmosphere.

Fresh commercial anhydrous THF and dimethylsulfate were used as such.

In a 1 L double-jacketed reactor equipped with a mechanical stirrer, a condenser, an addition funnel and a temperature probe were added 100 mL of dry THF and 6.9 mL of dimethylsulfate (9.14 g, 72 mmol, 2 eq.). A solution of 24.6 g of the esteramine (36 mmol, 1 eq.) in 154 mL of THF was preliminary prepared in the addition funnel and was progressively added into the reactor under stirring at room temperature in order to limit the temperature increase. The mixture was then stirred at room temperature under argon and the reaction progress was monitored by NMR analysis. After 2 hours the mixture was brought to 40° C. and 0.2 ml of dimethyl sulfate (2 mmol, 0.06 eq.) were added to allow stirring and to achieve complete conversion.

Reaction was completed after one hour of stirring at 40° C. and all the volatiles (THF and remaining DMS) were removed under vacuum in order to afford 33.15 g of a 95 mol % purity product as a beige wax with 94% yield.

NMR analysis showed the presence of 2 position isomers with 55:45 ratio between isomerized derivative (cis and trans diastereoisomers) and conjugated non-isomerized methylenated derivative.

$^{1}H$ NMR (MeOD, 400 MHz) δ (ppm): 5.60-5.25 (m, 1H: isomer 2 cis+trans), 4.80 (s, 1H, isomer 2 cis or trans), 4.75-4.50 (m, 4H, isomer 1+2), 4.38 (s, 1H, isomer 2 cis or trans), 3.84-3.72 (m, 4H, isomer 1+2), 3.69 (s, 6H, isomer 1+2), 3.22 (s, 18H, isomer 2), 3.21 (s, 18H, isomer 1), 2.50-2.35 (m, 4H, isomer 1), 2.22-2.02 (m, 4H, isomer 2 cis+trans), 1.60-1.09 (m, 35H, isomer 1+2), 0.90 (t, J=6.8 Hz, 6H).

$^{13}C$ NMR (MeOD, 101 MHz) δ (ppm): 169.22, 169.01, 168.96, 165.52, 134.16, 133.22, 132.94, 131.74, 65.90, 65.81, 60.23, 60.18, 59.73, 55.27, 54.66, 54.62, 35.66, 35.54, 33.24, 33.23, 31.76, 31.01, 30.94, 30.91, 30.87, 30.85, 30.77, 30.74, 30.71, 30.66, 30.65, 30.63, 30.60, 29.73, 29.62, 29.45, 29.27, 23.89, 14.61 (terminal $CH_3$).

Example 4—Synthesis of a Mixture of Quaternary Ammonium Compounds Wherein A is Represented by A-2 or A-3 (a Mixture of Compounds of Formula (V) and (VI)) Starting from $C_{23}$-12-Triocosanone Knoevenagel Condensation to Afford Diester Intermediate:

All the reactions were conducted in carefully dried vessels and under an inert argon atmosphere.

Fresh commercial anhydrous $CHCl_3$, anhydrous THF and anhydrous pyridine were used as such.

In a 1 L double-jacketed reactor equipped with a mechanical stirrer (propeller with four inclined plows), a condenser, an addition funnel and a temperature probe were added 48.6 mL of $TiCl_4$ (84.02 g, 0.443 mole), followed by 146 mL of $CHCl_3$. The mixture was stirred at −10° C. and anhydrous THF (358 mL) was slowly added through the addition funnel at a rate avoiding a temperature increase of the reaction medium above +5° C. During THF addition, a yellow precipitate appeared. Then 20.4 mL of dimethyl malonate (23.41 g, 0.177 mole) were added into the reaction mixture which was then allowed to stir at room temperature during 1 hour in order to allow malonate complexation to occur.

Then the mixture was allowed to cool down to 0° C. and a solution of 95.5 mL of anhydrous pyridine (93.44 g, 1.181 mole) in 23 mL of THF was slowly added to the reactor. During addition, the colour of the mixture turned red. The mixture was then allowed to stir at room temperature during 20 minutes to allow deprotonation to occur.

Finally, 50.00 g of $C_{23}$ ketone (0.148 mole) was added to the reaction mixture which was allowed to stir at room temperature during one night and during one more day at 35° C. 250 mL of water were then carefully added into the reactor followed by 250 mL of diethyl ether. The organic phase was separated and washed four times with 250 mL of water and one time with 200 mL of a saturated aqueous NaCl solution in order to remove pyridinium salts. The aqueous phases were collected and re-extracted with three times 250 mL of diethyl ether. The final organic phase was dried over $MgSO_4$, filtered and evaporated under vacuum to afford 69.5 g of crude orange oil. At this stage the crude contained residual amount of starting ketone as well as a main impurity corresponding to the condensation (aldolisation, crotonisation) of 2 equivalents of ketone.

The product could be easily purified by dissolving the oil in methanol (the by-product and the starting ketone being not soluble in methanol) followed by a filtration over celite.

The filtrate was evaporated to afford 54 g of oil with 95% of purity (RMN).

The overall purified yield was 77%.

$^{1}H$ NMR ($CDCl_3$, 400 MHz) δ (ppm): 3.72 (s, 6H), 2.33-2.29 (m, 4H), 1.48-1.40 (m, 4H), 1.34-1.17 (m, 32H), 0.85 (t, J=6.4 Hz, 6H).

$^{13}C$ NMR ($CDCl_3$, 101 MHz) δ (ppm): 166.28, 164.44, 123.63, 52.14, 34.6, 32.12, 30.13, 29.84, 29.73, 29.58, 29.55, 28.64, 22.90, 14.32 (terminal $CH_3$).

Transesterification with Dimethylaminoethanol to Afford Diamine Mixtures Intermediates:

All the reactions were conducted in carefully dried vessels and under an inert argon atmosphere.

Fresh commercial anhydrous toluene and dimethylaminoethanol were used as such. In a 1 L double-jacketed reactor equipped with a mechanical stirrer (propeller with four inclined plows), a condenser with a distillation apparatus and a temperature probe was added a solution of 51.1 g of the internal ketone/dimethyl malonate adduct (110 mmol, 1 eq.) in 300 mL of toluene. The mixture was stirred at room temperature and 45.5 mL of dimethylaminoethanol (40.5 g, 450 mmol, 4 eq.) was added to the reaction medium followed by 1.37 g of the catalyst dibutyltin oxide (5.5 mmol, 5 mol %).

Then the mixture was allowed to stir at 120° C. and the reaction progress was followed by NMR analysis. To run a proper analysis an aliquot of the reaction medium was sampled and diluted in diethyl ether, quenched with water, decanted and the organic phase was evaporated under vacuum to be analysed in $CDCl_3$ NMR solvent. After 2 days of stirring at 120° C. the mixture was allowed to cool down at room temperature and was concentrated under vacuum. 200 mL of water was then added to the residue followed by 200 mL of diethyl ether. The organic phase was decanted and washed three times with 300 mL of water and one time with 300 mL of a saturated aqueous solution of NaCl in order to remove excess of dimethylaminoethanol. The aqueous phases were collected and re-extracted with 700 mL of diethyl ether. The organic phases were collected and then dried over MgSO4, filtered and evaporated. The residue obtained was re-dissolved in methanol and the precipitated solid was filtered. The filtrate was evaporated to afford 59.04 g of crude yellow oil. At this stage the crude contained residual amount of the starting malonate and some by-products.

The product was then purified by flash chromatography on silica gel with an eluent consisting on $CHCl_3$/isopropanol mixture going through a gradient from 100% $CHCl_3$ to 100% isopropanol.

The clean fractions were collected, affording after solvent evaporation 22.9 g of a pure product corresponding to 35% isolated yield.

NMR analysis showed that the product is in the form of 2 position isomers mixture with the following ratio: 60 mol % of the isomerized product (cis and trans diastereoisomers) and 40 mol % of methylenated product.

$^1$H NMR ($CDCl_3$, 400 MHz) δ (ppm): 5.45-5.15 (m, 1H: isomer 2 cis+trans), 4.42 (s, 1H, isomer 2 cis or trans), 4.24-4.08 (m, 4H, isomer 1+2), 3.99 (s, 1H, isomer 2 cis or trans), 2.65-2.40 (m, 4H, isomer 1+2), 2.32-2.24 (m, 4H, isomer 1), 2.20 (s, 12H, isomer 1), 2.19 (s, 12H, isomer 2), 2.10-1.90 (m, 4H, isomer 2 cis+trans), 1.50-0.95 (m, 35H, isomer 1+2), 0.81 (t, J=6.4 Hz, 6H).

$^{13}$C NMR ($CDCl_3$, 101 MHz) δ (ppm): 168.81, 168.62, 165.71, 164.24, 132.27, 131.78, 131.33, 130.97, 123.95, 63.57, 62.98, 58.29, 57.69, 57.65, 53.71, 45.94, 34.66, 34.28, 32.13, 31.02, 30.23, 29.90, 29.87, 29.78, 29.65, 29.57, 29.55, 28.67, 28.64, 28.47, 28.29, 22.90, 14.33 (terminal $CH_3$).

Methylation to Afford Mixture of Compounds V and VI:

All the reactions were conducted in carefully dried vessels and under an inert argon atmosphere.

Fresh commercial anhydrous THF and dimethylsulfate were used as such.

In a 200 mL double-jacketed reactor equipped with a mechanical stirrer (propeller with four inclined plows), a condenser, an addition funnel and a temperature probe were added 100 mL of dry THF and 7.59 mL of dimethylsulfate (10.1 g, 80 mmol, 2 eq.). A solution of 22.94 g of the esteramine (40 mmol, 1 eq.) in 154 mL of THF was preliminary prepared in the addition funnel and was progressively added into the reactor under stirring at room temperature in order to limit the temperature increase. The mixture was then stirred at room temperature under argon and the reaction progress was monitored by NMR analysis. Reaction was completed after one hour of stirring at room temperature and all the volatiles (THF and remaining DMS) were removed under vacuum in order to afford 32.6 g of product as a beige wax with 99% yield.

NMR analysis showed the presence of two position isomers with 60:40 ratio between isomerized derivative (cis and trans diastereoisomers) and conjugated non-isomerized methylenated derivative.

$^1$H NMR (MeOD, 400 MHz) δ (ppm): 5.60-5.25 (m, 1H: isomer 2 cis+trans), 4.80 (s, 1H, isomer 2 cis or trans), 4.75-4.50 (m, 4H, isomer 1+2), 4.38 (s, 1H, isomer 2 cis or trans), 3.84-3.72 (m, 4H, isomer 1+2), 3.69 (s, 6H, isomer 1+2), 3.22 (s, 18H, isomer 2), 3.21 (s, 18H, isomer 1), 2.50-2.35 (m, 4H, isomer 1), 2.22-2.02 (m, 4H, isomer 2 cis+trans), 1.60-1.09 (m, 35H, isomer 1+2), 0.90 (t, J=6.8 Hz, 6H).

$^{13}$C NMR (MeOD, 101 MHz) δ (ppm): 169.22, 169.01, 168.96, 165.52, 134.16, 133.22, 132.94, 131.74, 65.90, 65.81, 60.23, 60.18, 59.73, 55.27, 54.66, 54.62, 35.66, 35.54, 33.24, 33.23, 31.76, 31.01, 30.94, 30.91, 30.87, 30.85, 30.77, 30.74, 30.71, 30.66, 30.65, 30.63, 30.60, 29.73, 29.62, 29.45, 29.27, 23.89, 14.61 (terminal $CH_3$).

Example 5—Synthesis of a Compound Wherein A is Represented by A-1, Specifically a Compound of Formula VII Starting from $C_{23}$ 12 Tricosanone Reductive Amination to Afford Primary Amine

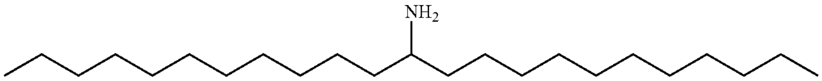 [SMILES: CCCCCCCCCCCC(N)CCCCCCCCCCC]

All the reactions were conducted under an inert argon atmosphere.

In a 5 L three necked round bottom flask equipped with a magnetic stirrer, a condenser, a temperature probe and a heater a solution of tricosan-12-one (100 g, 0.295 mol, 1 eq.) in 700 mL of methanol was prepared.

Then $NH_4OAc$ (227.386 g, 2.95 mol, 10 eq.) followed by $NaCNBH_3$ (74.15 g, 1.18 mol, 4 eq.) are added to the mixture in small portions. The reaction medium was stirred at room temperature for 1 hour. Finally, the mixture was heated under reflux during 16 hours. Then the reaction medium was cooled down to room temperature and concentrated under vacuum.

Finally, 500 mL of a saturated $NaHCO_3$ aqueous solution and 500 mL of methyl tert. butyl ether (MTBE) were added to the residue and the mixture was stirred at room temperature for one hour. Concentrated aqueous NaOH solution was added in order to adjust the pH to about 9. The product was extracted with MTBE and the organic phase was washed several times with water and brine. The organic phase was dried with $K_2CO_3$, filtered and concentrated in vacuum to afford 100.4 g of crude yellow oil.

The crude was then purified through flash chromatography column over silica gel using dichloromethane (DCM): methanol mixture as the eluent with a gradient going from DCM:MeOH=100:1 to DCM:MeOH=10:1+1% $Et_3N$. After solvent evaporation 93.5 g (0.275 mol) of pure light yellow oil was obtained.

Yield: 93%

Alkylation of Primary Amine to Afford Amino-Diester Intermediate

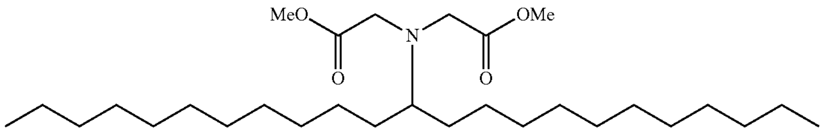 [SMILES: CCCCCCCCCCCC(CCCCCCCCCCC)N(CC(=O)OC)CC(=O)OC]

The reaction was carried out under an inert argon atmosphere.

In a 1 L round bottom flask equipped with a condenser, a temperature probe, a magnetic stirrer and a heater were added:

62.0 g (0.18 mol, 1 eq.) of the $C_{23}$ fatty primary amine.

700 mL of methyl-THF.

63.7 g of methyl 2-chloroacetate (0.59 mol, 3.3 eq.).

81.5 g of $K_2CO_3$ (0.59 mol, 3.3 eq.).

97.94 g of KI (0.59 mol, 3.3 eq.).

The mixture was then allowed to stir at reflux (78-80° C.) during one night.

At the end of the reaction the mixture was filtered and concentrated under vacuum to give 98.0 g of crude material that still contained methyl 2-chloroacetate.

The product was then purified by flash chromatography over silica gel using petroleum ether:ethyl acetate mixture (50:1) as the eluent to afford after solvent evaporation 52 g of pure material (0.108 mol).

Yield: 60%

Ester Hydrolysis to Afford Iminodiacetic Acid Intermediate.

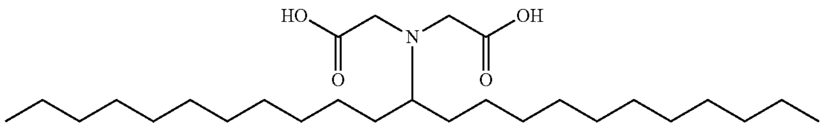 [SMILES: CCCCCCCCCCCC(CCCCCCCCCCC)N(CC(=O)O)CC(=O)O]

In a 2 L round bottom flask equipped with a magnetic stirrer were added:

27.3 g of NaOH (0.683 mol, 6.0 eq.)

300 mL of water 300 mL of methanol 300 mL of THF

The solution obtained was then allowed to stir at 0° C. and 55 g of the amino-diester (0.113 mol, 1 eq.) were slowly added.

The reaction medium was then stirred at room temperature overnight.

At the end of the reaction, the pH was adjusted from 11 to 1 by the addition of concentrated HCl solution and the product was extracted using two times 3 L of dichloromethane.

The organic phases were collected and washed several times with brine, dried over $MgSO_4$, filtered and the solvent was evaporated under vacuum to afford 55 g of product which was used as such for the next step.

Quantitative Yield

Esterification with Dimethylaminoethanol to Afford Diester Intermediate.

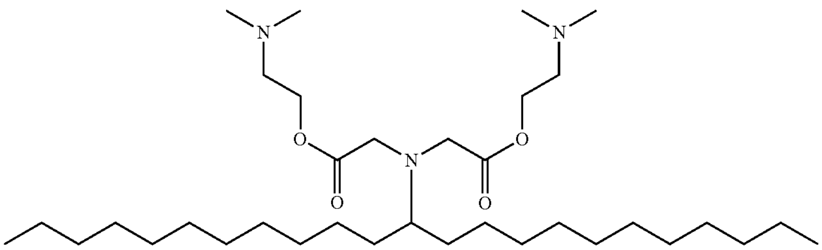 [SMILES: CCCCCCCCCCCC(CCCCCCCCCCC)N(CC(=O)OCCN(C)C)CC(=O)OCCN(C)C]

The reaction was carried out under an inert argon atmosphere.

In a 2 L round bottom flask equipped with a magnetic stirrer were added:

53.3 g (0.117 mol, 1 eq.) of the iminodiacetic acid intermediate

2 L of dichloromethane 104.2 g of dimethylaminoethanol (1.17 mole, 10 eq.)

142 g of trimethylamine (1.40 moles, 12 eq.)

189.7 g of HOBt (1.40 moles, 12 eq.)

The mixture was allowed to cool down to 0° C. and 220 g of EDCl (1.15 moles, 10 eq.) were added into the reaction vessel.

The mixture was allowed to stir at room temperature during twenty hours allowing the reaction to reach completion.

The reaction mixture was then washed with water and the organic phase was dried over $MgSO_4$, filtered and evaporated under vacuum to afford 118 g of crude product as dark yellow oil.

The crude material was then purified through flash chromatography over silica gel using first petroleum ether: CH2Cl2 mixture (9:1) as the eluent and then $CH_2Cl_2$: isopropanol (50:1)+1.5% $NEt_3$ mixture.

Two fractions were obtained: a first fraction containing 31.0 g of product and a second fraction containing 35 g of material.

The second fraction was then purified a second time to afford 29.2 g of deep yellow oil. Overall 60.2 g (101 mmoles) of pure product were obtained as a yellow oil.

Yield: 86%

Quaternization to Obtain Compound of Formula (VII)

All the reactions were conducted in carefully dried vessels and under an inert argon atmosphere.

Fresh commercial anhydrous THF and dimethylsulfate were used as such.

In a 200 mL double-jacketed reactor equipped with a mechanical stirrer (propeller with four inclined plows), a condenser, an addition funnel and a temperature probe were added 100 mL of dry THF and 8.0 mL of dimethylsulfate (10.6 g, 84 mmol, 2 eq.). A solution of 25.2 g of the esteramine (42 mmol, 1 eq.) in 154 mL of THF was prepared in the addition funnel and was progressively added to the reactor under stirring at room temperature in order to limit the temperature increase. The mixture was then stirred at room temperature under argon and the reaction progress was monitored by NMR analysis. Reaction was completed after one hour of stirring at room temperature and all the volatiles (THF and remaining DMS) were removed under vacuum in order to afford 35.7 g of product as a beige wax in quantitative yield.

$^1$H NMR (MeOD, 400 MHz) δ (ppm): 4.59-4.50 (m, 4H), 3.78-3.71 (m, 4H), 3.68 (s, 6H), 3.59-3.51 (brs, 4H), 3.25 (s, 18H), 2.68-2.54 (m, 1H), 1.60-1.00 (m, 40H), 0.90 (t, J=6.4 Hz, 6H).

$^{13}$C NMR (MeOD, 101 MHz) δ (ppm): 173.02, 66.13, 65.49, 59.35, 55.26, 54.69, 54.34, 33.23, 32.82, 31.04, 30.95, 30.93, 30.91, 30.63, 28.27, 23.89, 14.61 (terminal $CH_3$).

Example 6—Synthesis of a Compound Wherein A is Represented by A-1, Specifically a Compound of Formula VII Starting from $C_{31}$ 16-Hentriacontanone Reductive Amination to Afford Primary Amine.

Same protocol as described in Example 5 above for the C23 derivative was followed.

Alkylation of Primary Amine to Afford Amino-Diester Intermediate.

The reaction was carried out under an inert argon atmosphere.

In a 500 mL round bottom flask equipped with a condenser, a temperature probe, a magnetic stirrer and a heater were added:

18.0 g (40 mmoles, 1 eq.) of the $C_{31}$ fatty primary amine.

500 mL of methyl-THF.

12.48 g of methyl 2-chloroacetate (132 mmoles, 3.3 eq.).

18.24 g of $K_2CO_3$ (132 mmoles, 3.3 eq.).

21.92 g of KI (132 mol, 3.3 eq.).

The mixture was then allowed to stir at reflux (78-80° C.) during one night.

At the end of the reaction the mixture was filtered over a plug of celite. The solid was washed with THF and the filtrate was concentrated under vacuum to afford a crude material that still contained methyl 2-chloroacetate.

The product was then purified by flash chromatography over silica gel using petroleum ether:ethyl acetate mixture (100:1) as the eluent to afford after solvent evaporation 22.4 g of pure material (37.6 mmoles).

Yield: 94%

Ester Hydrolysis to Afford Imino-Diacetic Acid Intermediate.

In a 1 L round bottom flask equipped with a magnetic stirrer were added:

11.3 g of NaOH (0.282 mol, 6.0 eq.)

100 mL of water 100 mL of methanol 100 mL of THF

The solution obtained was then allowed to stir at 0° C. and 28 g of the amino-diester (0.047 mol, 1 eq.) was slowly added.

The reaction medium was then stirred at room temperature overnight.

At the end of the reaction, the pH was adjusted from 11 to 2 by the addition of 1M HCl aqueous solution and the product was extracted using dichloromethane.

The organic phases were collected and washed several times with brine and finally concentrated. The residue was redissolved in THF and the organic solution was dried over $MgSO_4$, filtered and the solvent was evaporated under vacuum to afford 26 g of product (45.8 mmoles) which was used as such for the next step.

Yield: 97%.

Esterification with Dimethylaminoethanol to Afford Diester Intermediate.

Same protocol as described in Example 5 for the $C_{23}$ derivative was followed.

Quaternization to Obtain Compound of Formula VII

Same protocol as described in Example 5 for the $C_{23}$ derivative was followed.

$^1$H NMR (MeOD, 400 MHz) δ (ppm): 4.52-4.36 (m, 4H), 3.71-3.61 (m, 4H), 3.58 (s, 6H), 3.46-3.39 (brs, 4H), 3.15 (s, 18H), 2.58-2.39 (m, 1H), 1.60-1.00 (m, 56H), 0.80 (t, J=6.8 Hz, 6H).

$^{13}$C NMR (MeOD, 101 MHz) δ (ppm): 173.09, 66.09, 65.23, 59.31, 55.25, 54.69, 54.29, 33.25, 32.82, 31.03, 30.99, 30.96, 30.91, 30.87, 30.66, 28.24, 28.13, 23.91, 14.68 (terminal $CH_3$).

Example 7—Synthesis of a Compound of Formula (VIII) Starting from 16-Hentriacontanone Reductive Amination to Afford Aminodiol Intermediate

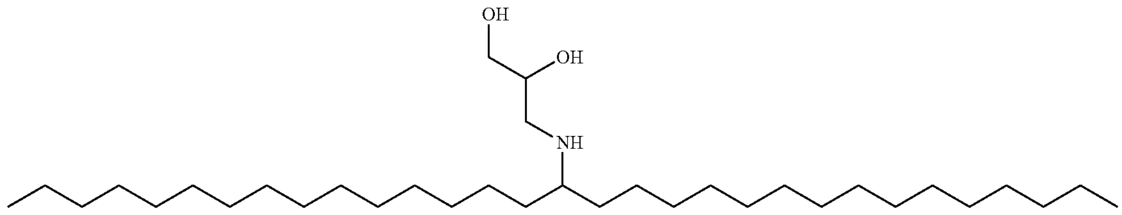 [SMILES: CCCCCCCCCCCCCCCC(CCCCCCCCCCCCCCC)NCC(O)CO]

The reaction was conducted under an inert argon atmosphere.

In a 1 L double-jacketed reactor equipped with a mechanical stirrer (propeller with four inclined plows), a condenser and a temperature probe were added:

50 g of 16-hentriacontanone (111 mmoles, 1 eq.)

281 mL of $CHCl_3$ 17.73 mL of 3-amino-1,2-propanediol (20.8 g, 222 mmoles, 2 eq.)

The mixture was then stirred at room temperature and 54.71 mL of $Ti(OEt)_4$ (59.52 g, 222 mmoles, 2 eq.) was added into the reactor. The mixture was then stirred at 65° C. overnight and it was observed that during the course of the reaction the mixture became homogeneous.

At the end of the reaction, the temperature was cooled down to 40° C. and 56 mL of anhydrous methanol was added into the reactor followed by the careful and slow addition of 8.74 g of $NaBH_4$ (222 mmoles, 2 eq.). Care was taken to avoid foaming during $NaBH_4$ addition.

The reaction medium was then stirred at 40° C. during three hours.

Then the mixture was cooled down to room temperature and 100 mL of water were added followed by 100 mL of diethyl ether. During water addition precipitation of $TiO_2$ occurred.

The suspension was filtered, the solid was washed several times with diethyl ether and the biphasic filtrate was separated. The organic phase was again filtered over celite and was washed with water and brine. The organic phase was then dried over $MgSO_4$, filtered and evaporated to afford the crude material as a yellow paste (48.9 g).

The crude was then purified through flash chromatography over silica gel using $CHCl_3$:isopropanol mixture as the eluent with a gradient going from 100:0 to 50:50.

After solvent evaporation 28.75 g of pure product was obtained (54.70 mmoles).

Yield: 49%

$^1H$ NMR (MeOD, 400 MHz) δ (ppm): 3.78-3.64 (m, 1H), 3.62-3.42 (m, 2H), 2.78 (dd, J=11.6 Hz, J=3.6 Hz, 1H), 2.62-2.40 (m, 2H), 1.70-1.11 (m, 56H), 0.90 (t, J=6.4 Hz, 6H).

$^{13}C$ NMR (MeOD, 101 MHz) δ (ppm): 71.78, 66.46, 59.03, 51.08, 34.67, 33.26, 31.08, 31.04, 30.97, 30.95, 30.92, 30.83, 30.80, 30.66, 26.87, 26.85, 23.91, 14.62 (terminal $CH_3$).

Esterification with Glycine Betaine to Afford Quaternary Ammonium Compound of Formula VIII All the reactions were conducted in carefully dried vessels and under an inert argon atmosphere.

Commercial anhydrous THF, anhydrous toluene and anhydrous CHCl3 stabilized with amylene were used as such.

Glycine betaine hydrochloride was dried through several washings with anhydrous THF followed by drying under vacuum prior to use.

In a 250 mL four necked round bottom flask equipped with a condenser, a distillation apparatus connected to a NaOH trap, a temperature probe, a magnetic stirrer and a heater were added:

7.13 g of betaine hydrochloride (46.4 mmol)

10 mL of $SOCl_2$ (16.38 g, 136.9 mmol) was then carefully introduced into the reactor vessel and the resulting suspension was progressively heated to 70° C. under stirring. It was observed that when the temperature reached 68° C., gas was released ($SO_2$ and HCl) and the mixture turned homogeneously yellow.

The mixture was then allowed to stir at 70° C. during two hours and hot anhydrous toluene (25 mL, 80° C.) was added into the vessel. The mixture was stirred and decanted at 0° C. to make the betainyl chloride precipitate. The upper phase of toluene was then removed through cannula and the operation of toluene washing was repeated four times in order to remove all $SOCl_2$ excess.

NMR analysis showed complete conversion of glycine betaine hydrochloride but also formation of $NMe_3$·HCl adduct ($NMe_3$·HCl content in the solid: 19.3 mol %).

20 mL of $CHCl_3$ was then added to the solid betainyl chloride.

A solution of the fatty diol (9.85 g, 18.7 mmol) in 30 mL of $CHCl_3$ was then prepared and was added dropwise to the betainyl chloride/$CHCl_3$ suspension at −3° C. at a rate avoiding the temperature of the reaction medium to go above 5° C. At the end of the addition the mixture was allowed to warm-up at room temperature and was then stirred at 50° C. for the night.

All the volatiles were then removed under vacuum at 30° C. to afford 16 g of a beige wax. NMR analysis showed that the purity of the resulting product is around 73 wt % (the remaining by-products are: protonated starting alcohol, $NMe_3$·HCl, betaine hydrochloride and mono-ester).

Yield: 75% (14 mmoles)

$^1H$ NMR ($CDCl_3$-MeOD, 400 MHz) δ (ppm): 5.55-5.63 (m, 1H), 4.93 (d, J=16.8 Hz, 1H), 4.92 (d, J=16.8 Hz, 1H), 4.81 (d, J=16.8 Hz, 1H), 4.70 (d, J=16.8 Hz, 1H), 4.49 (dd, J=12 Hz, J=3.6 Hz, 1H), 4.39 (dd, J=12 Hz, J=6.4 Hz, 1H), 3.36 (s, 9H), 3.33 (s, 9H), 3.32-3.28 (m, 2H), 1.80-1.45 (m, 4H), 1.45-1.10 (m, 52H), 0.84 (t, J=6.8 Hz, 6H).

$^{13}C$ NMR (MeOD, 101 MHz) δ (ppm): 166.06, 71.18, 65.29, 64.59, 64.28, 61.35, 54.99, 54.87, 45.99, 45.55, 33.24, 30.96, 30.93, 30.91, 30.80, 30.64, 30.61, 30.60, 26.34, 26.21, 23.89, 14.61 (terminal $CH_3$).

Example 8—Synthesis of a Quaternary Ammonium Compound Wherein A is Represented by A-5 and Corresponding to Formula (IX) Starting from $C_{31}$ 16-Hentriacontanone $C_{31}$ internal olefin was obtained from palmitic acid according to the protocol described in U.S. patent Ser. No. 10/035,746, example 4.

Epoxidation of Internal Olefin to Fatty Epoxide

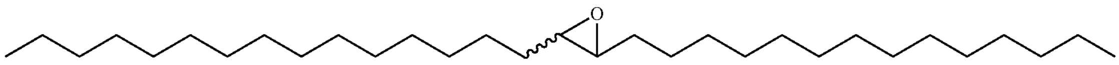 [SMILES: CCCCCCCCCCCCCCCC1OC1CCCCCCCCCCCCCC]

The reaction was conducted under an inert argon atmosphere.

In a 1 L double-jacketed reactor equipped with a mechanical stirrer (propeller with four inclined plows), a condenser, an addition funnel and a temperature probe were added 61.9 g of $C_{31}$ alkene (0.142 mol), followed by 16.3 ml (17.1 g, 0.285 mol) of acetic acid and 13.6 g (22 wt %) of Amberlite® IR 120H. The mixture was heated to 65° C. to melt the fatty alkene. The agitation was started and then 21.8 ml (24.2 g, 0.214 mol) of an aqueous solution of $H_2O_2$ (conc. 30%) was slowly added to the mixture using the addition funnel at a rate avoiding a significant temperature increase. This required about one hour.

The temperature was then increased to 75° C. and the reaction mixture was allowed to stir overnight (after 15 min, NMR analysis showed that the conversion level was already around 60% with 99% selectivity). Then additional 10.2 ml (11.3 g, 0.1 mol) of an aqueous solution of $H_2O_2$ (30%) was added slowly and after 4 hours following the second addition of $H_2O_2$ NMR analysis showed that the conversion level was around 88% (98% selectivity). Another addition of 8.14 ml of acetic acid (8.55 g, 0.142 mol) followed by 11.6 ml of 30% $H_2O_2$ (12.91 g, 0.114 mol) was finally performed in order to increase the conversion level.

The mixture was allowed to stir a second night at 75° C.

Finally NMR analysis showed a conversion level of 93% (95% selectivity).

The mixture was allowed to cool down to room temperature and then 300 ml of chloroform were added. The mixture was transferred to a separating funnel and the organic phase was washed three times with 300 ml of water and then the aqueous phase was extracted twice with 100 ml of chloroform. The Amberlite solid catalyst stayed in the aqueous phase and was removed during the first separation with the aqueous phase. The organic phases were collected, dried over $MgSO_4$, filtered and evaporated to give 65.3 g of a white solid with a purity of 91% w/w (epoxide+di-alcohol).

The yield taking into account the purity was 92%.

$^1H$ NMR ($CDCl_3$, 400 MHz) δ (ppm): 2.91-2.85 (m, 2H, diastereoisomer 1), 2.65-2.6 (m, 2H, diastereoisomer 2), 1.53-1.00 (m, 54H), 0.86 (t, J=6.8 Hz, 6H).

$^{13}C$ NMR ($CDCl_3$, 101 MHz) δ (ppm): 58.97, 57.28, 32.18, 31.96, 29.72, 29.6, 29.4, 27.86, 26.95, 26.63, 26.09, 22.72, 14.15 (terminal $CH_3$).

Hydrolysis of Fatty Epoxide to Afford Fatty Diol

The reaction was conducted under an inert argon atmosphere.

In a 1 L double-jacketed reactor equipped with a mechanical stirrer (propeller with four inclined plows), a condenser and a temperature probe were added 82.9 g of $C_{31}$ epoxide (purity: 94.5 wt %, 0.174 mol) followed by 480 mL of methyl-THF.

The mixture was allowed to stir at room temperature and 73 mL of a 3 M aqueous solution of $H_2SO_4$ was then added. The reaction medium was then stirred at 80° C. during 90 minutes. NMR analysis showed that the reaction was completed. The biphasic mixture was allowed to cool down to room temperature and the organic phase was separated. The solvent was then removed under vacuum and the residue was suspended in 200 ml of diethyl ether. The suspension was filtered and the resulting solid was washed 3 times with 50 mL of diethyl ether. The white solid was finally washed 2 times with 50 mL of methanol and was dried under vacuum to remove traces of solvent.

At the end 75.53 g of product was obtained as a white powder with a purity of 95.7% w/w corresponding to a yield of 89%.

$^1H$ NMR ($CDCl_3$, 400 MHz) δ (ppm): 3.61-3.55 (m, 2H, diastereoisomer 1), 3.43-3.25 (m, 2H, diastereoisomer 2), 1.88 (brd, J=2.4 Hz, OH, diastereoisomer 2), 1.72 (brd, J=3.2 Hz, OH, diastereoisomer 1), 1.53-1.10 (m, 54H), 0.86 (t, J=6.8 Hz, 6H).

$^{13}C$ NMR ($CDCl_3$, 101 MHz) δ (ppm): 74.71, 74.57, 33.66, 31.96, 31.23, 29.71, 29.39, 26.04, 25.68, 22.72, 14.15 (terminal $CH_3$)

Esterification of Fatty Diol with Trimethylglycine to Afford Compound of Formula IX All the reactions were conducted in carefully dried vessels and under an inert argon atmosphere.

Fresh commercial anhydrous $CHCl_3$ (amylene stabilized) and anhydrous toluene were used as such.

Betaine hydrochloride (19.66 g, 128.4 mmoles) was washed ten times with 20 ml of anhydrous THF followed by drying under vacuum to remove traces of solvent prior to use.

In a 100 ml four-neck round-bottom flask equipped with a magnetic stirrer, a heater, a condenser, a temperature probe and a curved distillation column connected to two traps of NaOH were quickly added:

19.66 g of dried betaine hydrochloride (128.4 mmoles) and 28 ml of $SOCl_2$ (45.86 g, 0.386 mol).

The heterogeneous mixture was stirred and the temperature was then slowly increased to 70° C. It was observed that when the temperature reached 68° C., gas was released ($SO_2$ and HCl) and the mixture turned homogeneous yellow.

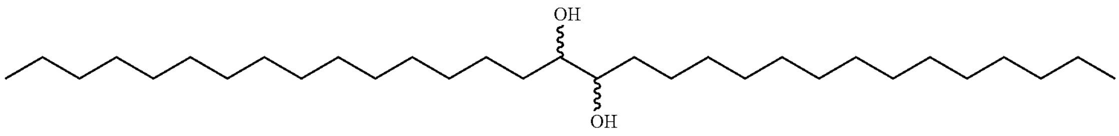 [SMILES: CCCCCCCCCCCCCCCC(O)C(O)CCCCCCCCCCCCCC]

The mixture was then allowed to stir at 70° C. during two hours and hot anhydrous toluene (25 mL, 80° C.) was added into the vessel. The mixture was stirred and then decanted at 0° C. (white-yellow precipitate formation) and the upper phase of toluene was removed through a cannula. The operation of toluene washing was repeated seven times in order to remove all $SOCl_2$ excess. NMR analysis showed complete conversion of glycine betaine hydrochloride but also formation of $NMe_3 \cdot HCl$ adduct ($NMe_3 \cdot HCl$ content in the solid: 12.3 mol %).

20 mL of dry $CHCl_3$ was then added to the solid betainyl chloride.

A solution of 26.19 g (56 mmol) of fatty diol in 90 ml of anhydrous $CHCl_3$ was prepared at 55° C. and was added dropwise under stirring to the reaction vessel at room temperature (exothermicity and emission of HCl was observed). The mixture was then allowed to stir at 55° C. overnight. Over the course of the reaction, the mixture turned homogeneously orange. NMR analysis showed that the conversion level was around 100%.

The mixture was then allowed to cool down to room temperature and the solvent was evaporated under vacuum.

The residue was solubilized in methanol at 0° C. and the formed precipitate was filtered out. The obtained filtrate was then evaporated to give 39.7 g of crude product.

This product was then deposited on a sinter filter and washed with cyclohexane to remove some remaining organic impurities. The resulting washed solid was dried under vacuum to afford 22 g of crude material. A final purification with a mixture of $CH_2Cl_2$/cyclohexane 50:50 was carried out; the solid was solubilized again in this solvent mixture at 50° C. and was allowed to cool down to room temperature. The formed precipitate was filtered out and after evaporation of the filtrate 19 g of a beige wax was obtained with the following composition:

95 wt % of glycine betaine diester
1.5 wt % of methyl betainate
2 wt % of trimethylamine hydrochloride
1.5 wt % of glycine betaine hydrochloride.

The purified yield was 44%.

$^1H$ NMR (MeOD-d4, 400 MHz) δ (ppm): 5.3-5.2 (m, 2H), 4.68 (d, J=16.8 Hz, 2H), 4.50 (d, J=16.8 Hz, 2H), 4.53 (s, 1H), 4.48 (s, 1H), 3.37 (s, 18H), 1.75-1.55 (m, 4H), 1.39-1.10 (m, 50H), 0.9 (t, J=6.8 Hz, 6H).

$^{13}C$ NMR (MeOD-d4, 101 MHz) δ (ppm): 164.58, 75.76, 62.43, 53.10, 31.68, 30.05, 29.41, 29.38, 29.33, 29.28, 29.15, 29.09, 28.96, 24.71, 22.34, 13.05 (terminal $CH_3$).

Example 9—Fabric Softening Formulations

TABLE 1

Example fabric softening formulations

| Ingredient | wt. % Composition Concentrate | Regular | Dilute |
|---|---|---|---|
| Fabric Softening active[1] | 20 | 9 | 4 |
| Perfume | 2.0 | 0.8 | 0.3 |
| Microcapsule | 2.5 | 0.5 | — |
| Tallow fatty alcohol (C16-C18) | — | — | 2 |
| Glycerol mono stearate | — | 3 | — |
| Fatty Acid C16-18 | 5 | — | — |
| Nonionic surfactant | — | 1.5 | 0.01 |
| Cationic polymer[2] | 0.2 | 0.2 | 0.2 |
| Silicone Antifoam | 0.05 | 0.05 | 0.1 |

TABLE 1-continued

Example fabric softening formulations

| Ingredient | wt. % Composition Concentrate | Regular | Dilute |
|---|---|---|---|
| Mirrors, dyes, pH regulators, preservatives etc. | <1 wt. % | <1 wt. % | <1 wt. % |
| Water | To 100 | To 100 | To 100 |

Fabric Softening active[1] - As synthesised in any of examples 1-8
Cationic polymer[2] - Flosoft 270LS ex. SNF The fabric softening compositions may be made by the following process:

Heat water in a vessel to –50° C., add the cationic polymer with stirring, followed by the mirrors and antifoam. Make a premix of quaternary ammonium at –65° C. and add to the main mix vessel with stirring. Add the fatty material and nonionic surfactant where present. Cool the mix to –35° C. and add the perfume ingredients.

Example 10—Softening Comparison

A novel ionic compound, made according to Example 8 herein, was compared to typical quaternary ammonium compounds having the general formula A:

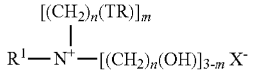

(A)

wherein each R is independently selected from a $C_{12}$ to $C_{20}$ alkyl or alkenyl group;
R1 represents a CH3,
T represents O—CO,
n is a number selected from 1 to 4,
m is a number selected from 1, 2, or 3,
and X— is a chlorine counter ion.

The softening compounds were prepared with a fatty co-softener in an aqueous solution:

| | Ingredeient wt. % in aqueous solution A | B | 1 | 2 |
|---|---|---|---|---|
| Typical quarternary amonium compound (A) | 2.67 | 2 | | 2 |
| Example 8 ionic compound | | | 2.67 | |
| Fatty Acid C16-18 | 1.33 | | 1.33 | |
| Tallow alcohol C16-C18 | | 2 | | 2 |
| Water | To 100 | To 100 | To 100 | To 100 |

The softening wash experiments were performed using a Terg-O-Tometer v2 under the following conditions:

Fabric: 40 g knotted cotton
Water volume: 1 litre
Water type: demineralised
Rinse time: 10 mins
Spin: 30 seconds
Temperature: Ambient (–20° C.)

The fabric was pre wet in the Terg-O-Tometer, removed and lightly squeezed to remove excess water. The softening compound solution was then pre-dispersed in the Terg-O-Tometer to provide 0.1% active (total of softening active and fatty co-softener). The pre-wetted fabric added back into the Terg-O-Tometer.

Following the rinse and spin cycles, the fabric was dried under 65% relative humidity at 20° C.

The relative hand value was assessed using a PhabrOmeter® ex. Nu Cybertek.

TABLE 2

Softening Results

| | Relative Hand Value |
|---|---|
| A | 0.66 |
| 1 | 2.07 |
| B | 0.72 |
| 2 | 1.43 |

A higher number indicates a softer fabric. The ionic compound prepared following Example 8, in combination with a fatty co-softener delivers improved softening, compared to a quaternary ammonium compound typically used in fabric softener formulations.

The invention claimed is:

1. A fabric softener composition comprising:

a. 1 to 20 wt. % ionic compound of general formula I:

(I)

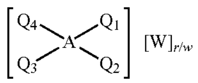

wherein

A is a tetravalent linker selected from the group consisting of A-1 to A-6

A-1

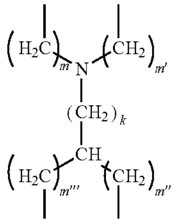

A-2

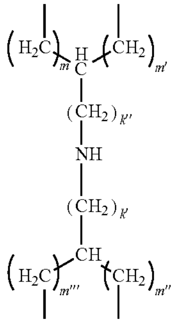

A-3

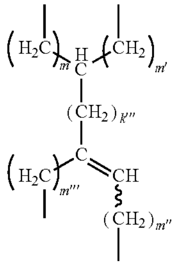

-continued

A-4

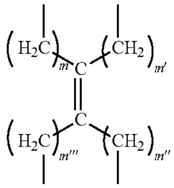

A-5

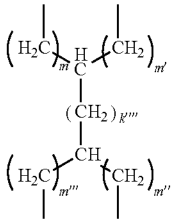

A-6

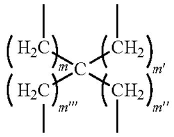

$Q_1$ to $Q_4$, which may be identical or different from each other, are selected from the group consisting of hydrogen, R and X, and W is an anion or an anionic group bearing w negative charges and r is the number of substituents $Q_1$ to $Q_4$ which are represented by a group X, wherein R, which may be the same or different at each occurrence, is a $C_5$-$C_{27}$ aliphatic group, m, m', m'' and m''', which may be the same or different at each occurrence, are 0, 1, 2 or 3, k, k', k'', k''' and k'''', which may be the same or different, are 0, 1, 2 or 3, and X, which may be the same or different at each occurrence, is represented by formula II (II)

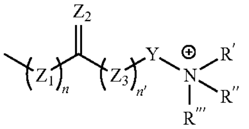

wherein $Z_1$, $Z_2$ and $Z_3$, are O, Y is a divalent $C_1$-$C_6$ aliphatic radical, R', R'' and R''', which may be the same or different, are hydrogen or a $C_1$ to $C_4$ alkyl group, the sum of n+n' being 2, wherein at least one of $Q_1$ to $Q_4$ is represented by X and at least two of groups $Q_1$ to $Q_4$ are represented by R, which groups R may be the same or different at each occurrence, and wherein, if the ionic compound is such that (i) A is represented by A-6 with m, in, m''' and m''' equal to 0, (ii) one and only one of $Q_1$ to $Q_4$ is represented by a substituent X and n in the substituent X is equal to 0 and (iii) two and only two of $Q_1$ to $Q_4$ are represented by substituents R, then the difference of the number of carbon atoms of the two substituents R is 0, 1, 3 or more than 3, b. 0.1 to 20 wt, % fatty co-softener; and c. water.

2. The fabric softener composition according to claim 1 wherein the ionic compound comprises one or two groups X and two and only two groups R.

3. The fabric softener composition according to claim 1 wherein the n' of the ionic compound is 1 and the Y of the ionic compound is a $C_2$-$C_6$ aliphatic group.

4. The fabric softener composition according to claim 1 wherein the A of the ionic compound is represented by A-6, m, m', m" and m'" are 0, $Z_1$ to $Z_3$ are 0 and wherein the ionic compound comprises two groups R and one group X.

5. The fabric softener composition according to claim 1 wherein the A of the ionic compound is represented by A-3 or A-4, m, m', m", m'" and k'" are 0 and two of substituents $Q_1$ to $Q_4$ are represented by groups X with both X attached to the same carbon atom of linker A and two groups R attached to the same or to different carbon atoms of linker A.

6. The fabric softener composition according to claim 1 wherein the A of the ionic compound represented by A-1, m and m' are 1, m" and m' are 0, k is 0 and two substituents $Q_1$ to $Q_4$ are represented by groups X with both groups X being attached to the nitrogen atom of linker A.

7. The fabric softener composition according to claim 1 wherein the A of the ionic compound represented by A-2, k" is 0, k" is 1, m is 1, m', m" and m'" are 0 and two of substituents $Q_1$ to $Q_4$ are represented by groups X attached to the same carbon atom of linker A.

8. The fabric softener composition according to claim 1 wherein the A of the ionic compound represented by A-5, m, m', m", m'" and k"" are 0, two of substituents $Q_1$ to $Q_4$ are X with each carbon atom of linker A carrying one group X and one group R wherein X and R might be the same or different at each occurrence.

9. The fabric softener composition according to claim 1, wherein the fatty co-softener is selected from fatty esters, fatty acids, fatty alcohols and combinations thereof.

10. The fabric softener composition according to claim 1 wherein the fabric softener comprises dye, antifoam and/or preservative.

11. A fabric softener composition comprising:

a. 1 to 20 wt. % ionic compound of general formula I:

(I)

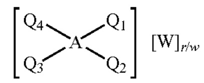

wherein

A is a tetravalent linker selected from the group consisting of A-1 to A-6

A-1

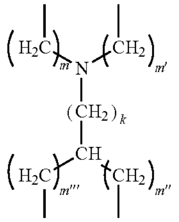

-continued

A-2

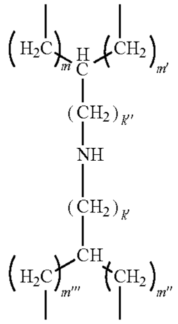

A-3

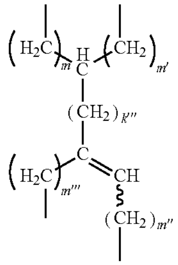

A-4

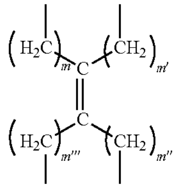

A-5

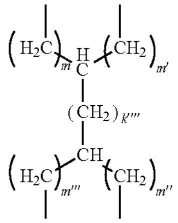

A-6

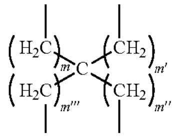

$Q_1$ to $Q_4$, which may be identical or different from each other, are selected from the group consisting of hydrogen, R and X, and W is an anion or an anionic group bearing w negative charges and r is the number of substituents $Q_1$ to $Q_4$ which are represented by a group X, wherein R, which may be the same or different at each occurrence, is a $C_5$-$C_{27}$ aliphatic group, m, m', m" and m'", which may be the same or different at each occurrence, are 0, 1, 2 or 3, k, k'k", k'" and k"", which may be the same or different, are 0, 1, 2 or 3, and X, which may be the same or different at each occurrence, is represented by formula II (II)

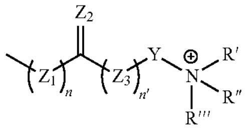

wherein $Z_1$, $Z_2$ and $Z_3$, are O, Y is are $CH_2$,

R', R" and R'", which may be the same or different, are hydrogen or a $C_1$ to $C_4$ alkyl group, n is 1, n' is 0, wherein at least one of $Q_1$ to $Q_4$ is represented by X and at least two of groups $Q_1$ to $Q_4$ are represented by R, which groups R may be the same or different at each occurrence, and wherein, if the ionic compound is such that (i) A is represented by A-6 with m, in, m'" and m'" equal to 0, (ii) one and only one of $Q_1$ to $Q_4$ is represented by a substituent X and n in the substituent X is equal to 0 and (iii) two and only two of $Q_1$ to $Q_4$ are represented by substituents R, then the difference of the number of carbon atoms of the two substituents R is 0, 1, 3 or more than 3, b. 0.1 to 20 wt, % fatty co-softener; and c. water.

* * * * *